US006107541A

United States Patent [19]

Arnold

[11] Patent Number: 6,107,541

[45] Date of Patent: Aug. 22, 2000

[54] PRAD1 TRANSGENIC MICE

[75] Inventor: Andrew Arnold, Newton, Mass.

[73] Assignee: The General Hospital Corporation, Boston, Mass.

[21] Appl. No.: 08/460,744

[22] Filed: Jun. 2, 1995

Related U.S. Application Data

[62] Division of application No. 07/667,711, Mar. 11, 1991.

[51] Int. Cl.[7] .......................... C12N 15/09; C12N 15/63; C12N 15/00; C12N 5/00

[52] U.S. Cl. ............................ 800/18; 800/10; 435/455; 435/325; 435/320.1; 435/69.1; 435/91.2

[58] Field of Search .................................. 800/2, 18, 10; 435/172.3, 69.1, 91.2, 325, 320.1, 455; 424/93.21; 536/23.1, 24.31

[56] References Cited

U.S. PATENT DOCUMENTS

| | | | |
|---|---|---|---|
| 4,786,718 | 11/1988 | Weinberg et al. | 530/387 |
| 5,118,615 | 6/1992 | Matsuo et al. | 435/69.1 |

OTHER PUBLICATIONS

Robles et al., PNAS, vol. 93, No. 15, pp. 7634–7638, Jul. 23, 1996.

Wang et al., Nature, vol. 369 (6482), pp. 669–671, Jun. 23, 1994.

Houdebine, Journal of Biotechnology, vol. 34, pp. 269–287, 1994.

Strojek & Wagner, Genetic Engineering: Principles and Methods, vol. 10, pp. 221–246, 1988.

Lozano et al., Molecular Carcinogenesis, vol. 4, pp. 3–9, 1991.

Arnold, A., et al., "Monoclonality and Abnormal Parathyroid Hormone Genes in Parathyroid Adenomas," *New Engl. J. Med. 318*(*11*):658–662 (Mar. 17, 1988).

Arnold, A., et al., "Molecular Cloning and Chromosomal Mapping of DNA Rearranged With the Parathyroid Hormone Gene in a Parathyroid Adenoma," *J. Clin. Invest. 83*(*6*):2034–2040 (Jun. 1989).

Arnold, A., et al., "DNA Rearranged Adjacent to the PTH Gene in a Parathyroid Adenoma Encodes an Abnormally Expressed Gene," *J. Bone Min. Res. 4* (*Suppl. 1*):s262, Abstr. No. 579 1989).

Arnold, A., et al., "Parathyroid Adenomas. Clonality in Benign Neoplasia," in: *Molecular Genetics in Cancer Diagnosis,* Cossman, J., ed., New York: Elsevier Science Publishing Co., Inc., pp. 399–408 (1990).

Bale, A.E., et al., "The Parathyroid Adenoma Breakpoint Sequence in 11q13 Maps Close to BCL1 and is not a Candidate Gene for MEN1," *Am. J. Human Genet. 47*(*3*):A3, Abstract No. 0002 (1990).

Bale, S.J., et al., "Linkage Analysis of Multiple Endocrine Neoplasia Type 1 with INT2 and Other Markers on Chromosome 11," *Genomics 4*(*3*):320–322 (Apr. 1989).

Cross, F.R. "DAF1, a Mutant Gene Affecting Size Control, Pheromone Arrest, and Cell Cycle Kinetics of *Saccharomyces cerevisiae," Molec. Cell. Biol. 8*(*11*):4675–4684 (Nov. 1988).

Draetta, G., et al., "Cdc2 Protein Kinase is Complexed With Both Cyclin A and B: Evidence for Proteolytic Inactivation of MPF," *Cell 56*(*5*): 829–838 (Mar. 10, 1989).

Evans, T., et al., "Cyclin: A Protein Specified by Maternal mRNA in Sea Urchin Eggs That is Destroyed at Each Cleavage Division," *Cell 33*(*2*):389–396 (Jun. 1983).

Friedman, E., et al., "Genetic Abnormalities in Sporadic Parathyroid Adenomas," *J. Clin. Endocrinol. Metab. 71*(*2*):293–297 (Aug. 1990).

Hunt, T., "Cell Biology. Cell Cycle Gets More cyclins," *Nature 350*:462–463 (Apr. 11, 1991).

Lew, D.J., et al., "Isolation of Three Novel Human Cyclins by Rescue of G1 Cyclin (CLn) Function in Yeast," *Cell 66*(*6*):1197–1206 (Sep. 20, 1991).

Matsushime, H., et al., "Colony–Stimulating Factor 1 Regulates Novel Cyclins During the G1 Phase of the Cell Cycle," *Cell 65*(*4*):701–713 (May 17, 1991).

Minshull, J., et al., "The A– and B–Type Cyclin Associated cdc2 Kinases in Xenopus Turn On and Off at Different Times in the Cell Cycle," *EMBO J. 9*(*9*):2865–2875 (Sep. 1990).

Motokura, T., et al., "A Novel Cyclin Encoded by a bc11–Linked Candidate Oncogene," *Nature 350*:512–515 (Apr. 11, 1991).

Murray, A.W., and Kirschner, M.W., "Dominoes and Clocks: The Union of Two Views of the Cell Cycle," *Science 246*:614–621 (Nov. 3, 1989).

Nash, R., et al., "The WHI1$^{+}$ Gene of *Saccharomyces cerevisiae* Tethers Cell Division to Cell Size and Is a Cyclin Homolog," *EMBO J. 7*(*13*):4335–4346 (Dec. 20, 1988).

Nasmyth, K.A., "FAR–Reaching Discoveries About the Regulation of START," *Cell 63*(*6*):1117–1120 (Dec. 21, 1990).

Nurse, P., "Universal Control Mechanism Regulating Onset of M–Phase," *Nature 344*:503–508 (Apr. 5, 1990).

Pines, J., and Hunter, T., "Isolation of a Human Cyclin cDNA: Evidence for Cyclin mRNA and Protein Regulation in the Cell Cycle and for Interaction With p34cdc2," *Cell 58*(*5*):833–846 (Sep. 8, 1989).

Pines, J., and Hunter, T., "Human Cyclin A is Adenovirus E1A–Associated Protein p60 and Behaves Differently from Cyclin B," *Nature 346*:760–763 (Aug. 23, 1990).

(List continued on next page.)

*Primary Examiner*—Scott D. Priebe
*Assistant Examiner*—Jill D. Martin
*Attorney, Agent, or Firm*—Sterne, Kessler, Goldstein & Fox P.L.L.C.

[57] ABSTRACT

The invention relates to isolated nucleic acid sequences encoding PRAD1, and fragments thereof. The invention further relates to transgenic mice bearing a transgene which includes a nucleic acid sequence encoding PRAD 1 under transcriptional control of a heterologous promoter, and cells or cell lines derived from such an mice.

7 Claims, 18 Drawing Sheets

OTHER PUBLICATIONS

Raffeld, M., and Jaffe, E.S., "bcl–1, t(11;14), and Mantle Cell–Derived Lymphomas," *Blood 78*(*2*):259–263 (Jul. 15, 1991).

Rosenberg, C.L., et al., "Rearrangement and Overexpression of D11S287E, a Candidate Oncogene on Chromosome 11q13 in Benign Parathyroid Tumors," *Oncogene 6*(*3*):449–454, BIOSIS Abstract No. 91131959 (Mar., 1991).

Rosenberg, C.L., et al., "PRAD1, a Candidate BCL1 Oncogene: Mapping and Expression in Centrocytic Lymphoma," *Proc. Natl. Acad. Sci. USA 88*(*21*):9638–9642, BIOSIS Abstract No. 93018797 (Nov. 1, 1991).

Sambrook, J., et al., *Molecular Cloning: a Laboratory Manual,* 2nd Ed., Cold Spring Harbor, NY: Cold Spring Harbor Laboratory Press, pp. 18.76, 18.81 (1989).

Swenson, K.I., et al., "The Clam Embryo Protein Cyclin A Induces Entry into M Phase and the Resumption of Meiosis in Xenopus Oocytes," *Cell 47*(*6*):861–870 (Dec. 26, 1986).

Vasicek, T.J., et al., "Nucleotide Sequence of the Human Parathyroid Hormone Gene," *Proc. Natl. Acad. Sci. USA 80*(*8*):2127–2131 (Apr. 1983).

Wang, J., et al., "Hepatitis B Virus Integration in a Cyclin A Gene in a Hepatocellular Carcinoma," *Nature 343*:555–557 (Feb. 8, 1990).

Westendorf, J.M., et al., "The Role of Cyclin B in Meiosis I," *J. Cell Biol. 108*(*4*):1431–1444 (Apr. 1989).

Withers, D.A., et al., "Characterization of a Candidate bcl–1 Gene," *Molec. Cell. Biol. 11*(*10*):4846–4853 (Oct. 1991).

Xiong, Y., et al., "Human D–Type Cyclin," *Cell 65*(*4*):691–699 (May 17, 1991).

Copy of the International Search Report for PCT Application No. PCT/US92/01925, which corresponds to US Application No. 07/667,711, the parent of the captioned application.

Copy of the Written Opinion from the International Searching Authority for PCT Application No. PCT/US92/01925, which corresponds to US Application No. 07/667,711, the parent of the captioned application.

```
GGCGCAGTAG CAGCGAGCAG CAGAGTCCGC ACGCTCCGGC GAGGGGCAGA AGAGCGCGAG    60

GGAGCGCGGG GCAGCAGAAG CGAGAGCCGA GCGCGGACCC AGCCAGGACC CACAGCCCTC   120

CCCAGCTGCC CAGGAAGAGC CCCAGCC ATG GAA CAC CAG CTC CTG TGC TGC       171
                              Met Glu His Gln Leu Leu Cys Cys
                               1               5

GAA GTG GAA ACC ATC CGC CGC GCG TAC CCC GAT GCC AAC CTC CTC AAC     219
Glu Val Glu Thr Ile Arg Arg Ala Tyr Pro Asp Ala Asn Leu Leu Asn
     10                  15                  20

GAC CGG GTG CTG CGG GCC ATG CTG AAG GCG GAG GAG ACC TGC GCG CCC     267
Asp Arg Val Leu Arg Ala Met Leu Lys Ala Glu Glu Thr Cys Ala Pro
 25                  30                  35                  40

TCG GTG TCC TAC TTC AAA TGT GTG CAG AAG GAG GTC CTG CCG TCC ATG     315
Ser Val Ser Tyr Phe Lys Cys Val Gln Lys Glu Val Leu Pro Ser Met
             45                  50                  55

CGG AAG ATC GTC GCC ACC TGG ATG CTG GAG GTC TGC GAG GAA CAG AAG     363
Arg Lys Ile Val Ala Thr Trp Met Leu Glu Val Cys Glu Glu Gln Lys
         60                  65                  70

TGC GAG GAG GAG GTC TTC CCG CTG GCC ATG AAC TAC CTG GAC CGC TTC     411
Cys Glu Glu Glu Val Phe Pro Leu Ala Met Asn Tyr Leu Asp Arg Phe
     75                  80                  85
```

FIG.6A

```
CTG TCG CTG GAG CCC GTG AAA AAG AGC CGC CTG CAG CTG CTG GGG GCC     459
Leu Ser Leu Glu Pro Val Lys Lys Ser Arg Leu Gln Leu Leu Gly Ala
     90                  95                 100

ACT TGC ATG TTC GTG GCC TCT AAG ATG AAG GAG ACC ATC CCC CTG ACG     507
Thr Cys Met Phe Val Ala Ser Lys Met Lys Glu Thr Ile Pro Leu Thr
105                 110                 115                 120

GCC GAG AAG CTG TGC ATC TAC ACC GAC AAC TCC ATC CGG CCC GAG GAG     555
Ala Glu Lys Leu Cys Ile Tyr Thr Asp Asn Ser Ile Arg Pro Glu Glu
            125                 130                 135

CTG CTG CAA ATG GAG CTG CTC CTG GTG AAC AAG CTC AAG TGG AAC CTG     603
Leu Leu Gln Met Glu Leu Leu Leu Val Asn Lys Leu Lys Trp Asn Leu
        140                 145                 150

GCC GCA ATG ACC CCG CAC GAT TTC ATT GAA CAC TTC CTC TCC AAA ATG     651
Ala Ala Met Thr Pro His Asp Phe Ile Glu His Phe Leu Ser Lys Met
        155                 160                 165

CCA GAG GCG GAG GAG AAC AAA CAG ATC ATC CGC AAA CAC GCG CAG ACC     699
Pro Glu Ala Glu Glu Asn Lys Gln Ile Ile Arg Lys His Ala Gln Thr
    170                 175                 180

TTC GTT GCC CTC TGT GCC ACA GAT GTG AAG TTC ATT TCC AAT CCG CCC     747
Phe Val Ala Leu Cys Ala Thr Asp Val Lys Phe Ile Ser Asn Pro Pro
185                 190                 195                 200
```

FIG.6B

```
TCC ATG GTG GCA GCG GGG AGC GTG GTG GCC GCA GTG CAA GGC CTG AAC       795
Ser Met Val Ala Ala Gly Ser Val Val Ala Ala Val Gln Gly Leu Asn
                205                 210                 215

CTG AGG AGC CCC AAC AAC TTC CTG TCC TAC TAC CGC CTC ACA CGC TTC       843
Leu Arg Ser Pro Asn Asn Phe Leu Ser Tyr Tyr Arg Leu Thr Arg Phe
            220                 225                 230

CTC TCC AGA GTG ATC AAG TGT GAC CCA GAC TGC CTC CGG GCC TGC CAG       891
Leu Ser Arg Val Ile Lys Cys Asp Pro Asp Cys Leu Arg Ala Cys Gln
        235                 240                 245

GAG CAG ATC GAA GCC CTG CTG GAG TCA AGC CTG CGC CAG GCC CAG CAG       939
Glu Gln Ile Glu Ala Leu Leu Glu Ser Ser Leu Arg Gln Ala Gln Gln
    250                 255                 260

AAC ATG GAC CCC AAG GCC GCC GAG GAG GAG GAA GAG GAG GAG GAG GAG       987
Asn Met Asp Pro Lys Ala Ala Glu Glu Glu Glu Glu Glu Glu Glu Glu
265                 270                 275                 280

GTG GAC CTG GCT TGC ACA CCC ACC GAC GTG CGG GAC GTG GAC ATC TGA      1035
Val Asp Leu Ala Cys Thr Pro Thr Asp Val Arg Asp Val Asp Ile
                285                 290                 295

GGGCGCCAGG CAGGCGGGCG CCACCGCCAC CCGCAGCGAG GGCGGAGCCG GCCCCAGGTG    1095

CTCCACTGAC AGTCCCTCCT CTCCGGAGCA TTTTGATACC AGAAGGGAAA GCTTCATTCT    1155
```

FIG.6C

```
CCTTGTTGTT GGTTGTTTTT TCCTTTGCTC TTTCCCCCTT CCATCTCTGA CTTAAGCAAA   1215
AGAAAAAGAT TACCCAAAAA CTGTCTTTAA AAGAGAGAGA GAGAAAAAAA AAATAGTATT   1275
TGCATAACCC TGAGCGGTGG GGGAGGAGGG TTGTGCTACA GATGATAGAG GATTTTATAC   1335
CCCAATAATC AACTCGTTTT TATATTAATG TACTTGTTTC TCTGTTGTAA GAATAGGCAT   1395
TAACACAAAG GAGGCGTCTC GGGAGAGGAT TAGGTTCCAT CCTTTACGTG TTTAAAAAAA   1455
AGCATAAAAA CATTTTAAAA ACATAGAAAA ATTCAGCAAA CCATTTTTAA AGTAGAAGAG   1515
GGTTTTAGGT AGAAAAACAT ATTCTTGTGC TTTTCCTGAT AAAGCACAGC TGTAGTGGGG   1575
TTCTAGGCAT CTCTGTACTT TGCTTGCTCA TATGCATGTA GTCACTTTAT AAGTCATTGT   1635
ATGTTATTAT ATTCCGTAGG TAGATGTGTA ACCTCTTCAC CTTATTCATG GCTGAAGTCA   1695
CCTCTTGGTT ACAGTAGCGT AGCGTGGCCG TGTGCATGTC CTTTGCGCCT GTGACCACCA   1755
CCCCAACAAA CCATCCAGTG ACAAACCATC CAGTGGAGGT TTGTCGGGCA CCAGCCAGCG   1815
TAGCAGGGTC GGGAAAGGCC ACCTGTCCCA CTCCTACGAT ACGCTACTAT AAAGAGAAGA   1875
CGAAATAGTG ACATAATATA TTCTATTTTT ATACTCTTCC TATTTTTGTA GTGACCTGTT   1935
TATGAGATGC TGGTTTTCTA CCCAACGGCC CTGCAGCCAG CTCACGTCCA GGTTCAACCC   1995
```

FIG.6D

```
ACAGCTACTT GGTTTGTGTT CTTCTTCATA TTCTAAAACC ATTCCATTTC CAAGCACTTT   2055
CAGTCCAATA GGTGTAGGAA ATAGCGCTGT TTTTGTTGTG TGTGCAGGGA GGGCAGTTTT   2115
CTAATGGAAT GGTTTGGGAA TATCCATGTA CTTGTTTGCA AGCAGGACTT TGAGGCAAGT   2175
GTGGGCCACT GTGGTGGCAG TGGAGGTGGG GTGTTTGGGA GGCTGCGTGC CAGTCAAGAA   2235
GAAAAAGGTT TGCATTCTCA CATTGCCAGG ATGATAAGTT CCTTTCCTTT TCTTTAAAGA   2295
AGTTGAAGTT TAGGAATCCT TTGGTGCCAA CTGGTGTTTG AAAGTAGGGA CCTCAGAGGT   2355
TTACCTAGAG AACAGGTGGT TTTTAAGGGT TATCTTAGAT GTTTCACACC GGAAGGTTTT   2415
TAAACACTAA AATATATAAT TTATAGTTAA GGCTAAAAAG TATATTTATT GCAGAGGATG   2475
TTCATAAGGC CAGTATGATT TATAAATGCA ATCTCCCCTT GATTTAAACA CACAGATACA   2535
CACACACACA CACACACACA CACAAACCTT CTGCCTTTGA TGTTACAGAT TTAATACAGT   2595
TTATTTTTAA AGATAGATCC TTTTATAGGT GAGAAAAAAA CAATCTGGAA GAAAAAAACC   2655
ACACAAAGAC ATTGATTCAG CCTGTTTGGC GTTTCCCAGA GTCATCTGAT TGGACAGGCA   2715
TGGGTGCAAG GAAAATTAGG GTACTCAACC TAAGTTCGGT TCCGATGAAT TCTTATCCCC   2775
TGCCCCTTCC TTTAAAAAAC TTAGTGACAA AATAGACAAT TTGCACATCT TGGCTATGTA   2835
```

FIG.6E

```
ATTCTTGTAA TTTTTATTTA GGAAGTGTTG AAGGGAGGTG GCAAGAGTGT GGAGGCTGAC   2895
GTGTGAGGGA GGACAGGCGG GAGGAGGTGT GAGGAGGAGG CTCCCGAGGG GAAGGGGCGG   2955
TGCCCACACC GGGGACAGGC CGCAGCTCCA TTTTCTTATT GCGCTGCTAC CGTTGACTTC   3015
CAGGCACGGT TTGGAAATAT TCACATCGCT TCTGTGTATC TCTTTCACAT TGTTTGCTGC   3075
TATTGGAGGA TCAGTTTTTT GTTTTACAAT GTCATATACT GCCATGTACT AGTTTTAGTT   3135
TTCTCTTAGA ACATTGTATT ACAGATGCCT TTTTTGTAGT TTTTTTTTTT TTTATGTGAT   3195
CAATTTTGAC TTAATGTGAT TACTGCTCTA TTCCAAAAAG GTTGCTGTTT CACAATACCT   3255
CATGCTTCAC TTAGCCATGG TGGACCCAGC GGGCAGGTTC TGCCTGCTTT GGCGGGCAGA   3315
CACGCGGGCG CGATCCCACA CAGGCTGGCG GGGGCCGGCC CCGAGGCCGC GTGCGTGAGA   3375
ACCGCGCCGG TGTCCCCAGA GACCAGGCTG TGTCCCTCTT CTCTTCCCTG CGCCTGTGAT   3435
GCTGGGCACT TCATCTGATC GGGGGCGTAG CATCATAGTA GTTTTTACAG CTGTGTTATW   3495
CTTTGCGTGT AGCTATGGAA GTTGCATAAT TATTATTATT ATTATTATAA CAAGTGTGTC   3555
TTACGTGCCA CCACGGCGTT GTACCTGTAG GACTCTCATT CGGGATGATT GGAATAGCTT   3615
CTGGAATTTG TTCAAGTTTT GGGTATGTTT AATCTGTTAT GTACTAGTGT TCTGTTTGTT   3675
```

FIG.6F

```
ATTGTTTTGT TAATTACACC ATAATGCTAA TTTAAAGAGA CTCCAAATCT CAATGAAGCC   3735
AGCTCACAGT GCTGTGTGCC CCGGTCACCT AGCAAGCTGC CGAACCAAAA GAATTTGCAC   3795
CCCGCTGCGG GCCCACGTGG TTGGGGCCCT GCCCTGGCAG GGTCATCCTG TGCTCGGAGG   3855
CCATCTCGGG CACAGGCCCA CCCCGCCCCA CCCCTCCAGA ACACGGCTCA CGCTTACCTC   3915
AACCATCCTG GCTGCGGCGT CTGTCTGAAC CACGCGGGGG CCTTGAGGGA CGCTTTGTCT   3975
GTCGTGATGG GGCAAGGGCA CAAGTCCTGG ATGTTGTGTG TRTCGAGAGG CCAAAGGCTG   4035
GTGGCAAGTG CACGGGGCAC AGCGGAGTCT GTCCTGTGAC GCGCAAGTCT GAGGGTCTGG   4095
GCGGCGGGCG GCTGGGTCTG TGCATTTCTG GTTGCACCGC GGCGCTTCCC AGCACCAACA   4155
TGTAACCGGC ATGTTTCCAG CAGAAGACAA AAAGACAAAC ATGAAAGTCT AGAAATAAAA   4215
CTGGTAAAAC CCCAAAAAAA AAAAAAAAA                                     4244
```

FIG.6G

```
human cyclin A: MRAILVDWLVEVGEEYKLQNETLHLAVNYIDRFLSSMSVLRGKLQLVGTAAMLLASKFEEIYPPEVAEFVYITDDTYTK  288
                || |*  |**|| || | **|   ||*||*|||||  *| ***|||*|** | *|||  |  |          ||**
pradl:          MRKIVATWMLEVCEEQKCEEEVFPLAMNYLDRFLSLEPVKKSRLQLLGATCMFVASKMKETIPLTAEKLCIYTDNSIRP  134
                || |*  |**|| ||*|   |   |**||*|||||  *| ***|||*||* ||*|*|  |  |          ||**  *
clam cyclin A:  MRCILVDWLVEVSEEDKLHRETLFLGVNYIDRFLSKISVLRGKLQLVGAASMFLAAKYEEIYPPDVKEFAYITDDTYTS  273

human cyclin A: KQVLRMEHLVLKVLTFDLAAPTVNQFLTQYFLHQQPANCKVESL...AMFLGELSLIDADPYLKYLPSVIAGAA  359
                 **| || |**  | **||| |  *|*  *  *   |*   * *   |      |    |    **   ||**|***
pradl:          EELLQMELLLVNKLKWNLAAMTPHDFIEHFLSKMPEAEENKQIIRKHAQTFVALCATDVK.FISNPPSMVAAGS  207
                ***| || |**  | ***|  |*  | | || |  *|**    **  *      |    |*  **    ||* ||**
clam cyclin A:  QQVLRMEHLILKVLTFDVAVPTTNWFCEDFL.KSCDADDK...LKSLTMFLTELTLIDMDAYLKYLPSITAAAA  343

human cyclin B: MRAILIDWLVQVQMKFRLLQETMYMTVSIIDRFMQNNCVPKKMLQLVGVTAMFIASKYEEMYPPEIGDFAFVTDNTYTK  279
                || |*  |***|    *  *|   ***  *|||*  * | |  |||*| | ||*|||  |  |          |||*
pradl:          MRKIVATWMLEVCEEQKCEEEVFPLAMNYLDRFLSLEPVKKSRLQLLGATCMFVASKMKETIPLTAEKLCIYTDNSIRP  134
                || |** |**||     *    |    ||*| *||||||         *|||*| * *|*|||  | *  * *      *| *
cdc13:          MRGILTDWLIEVHSRFRLLPETLFLAVNIIDRFLSLRVCSLNKLQLVGIAALFIASKYEEVMCPSVQNFVYMADGGYDE  313

human cyclin B: HQIRQMEMKILRALNFGLGRPLPLHFLRR.ASKIGEVDVEQHTL...AKYLMELTMLDYDMVHFPPSQIAAGA  348
                 ** |||* **  | * |*   |   |*    ||* | * *    *    |    * |    |    *   ||| *|||*
pradl:          EELLQMELLLVNKLKWNLAAMTPHDFIEHFLSKMPEAEENKQIIRKHAQTFVALCATDVKFISNPPSMVAAGS  207
                ||*|| |   **   | *|||    | *     || *** |*         |   |    | *    | | ** |||    |**
cdc13:          EEILQAERYILRVLEFNLAYPNPMN....FLRRISKADFYDIQTRTVAKYLVEIGLLDHKLLPYPPSQQCAAA  382

pradl:          MRKIVATWMLEVCEEQKCEEEVFPLAMNYLDRFLSLEPVKKSRLQLLGATCMFVASKMKETIPLTA.....EKLCIYTD  129
                || **  ***                |*   ||** |    *|     |||* | ****||  **      |        * ||   *
cln3:           MRFLIFDFIMYCHTRLNLSTSTLFLTFTILDKYSSRFIIKSYNYQLLSLTALWISSKFWDSKNRMATLKVLQNLC.CNQ  184

pradl:          NSIRPEELLQMELLLVNKLKWNLAAMTPHD.FIEHFLSKMPEAEENKQIIRKHAQTFVALCATDVKFISNPPSMVAAGS  207
                 ||*  *    ||* |    | | *   ** | *|* ||    * *      **     * *  |       *  * |***       *
cln3:           YSIK..QFTTMEMHLFKSLDWSICQSATFDSYIDIFLFQSTSPLSPGVVL...SAPLEAFIQQKLALLNNAAGTAINKS  258
```

FIG. 7

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
(A) LENGTH: 4244 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 148..1035

(xi) SEQUENCE DESCRIPTION: SEQ ID NO:1:

```
GGCGCAGTAG CAGCGAGCAG CAGAGTCCGC ACGCTCCGGC GAGGGGCAGA AGAGCGCGAG     60

GGAGCGCGGG GCAGCAGAAG CGAGAGCCGA GCGCGGACCC AGCCAGGACC CACAGCCCTC    120

CCCAGCTGCC CAGGAAGAGC CCCAGCC ATG GAA CAC CAG CTC CTG TGC TGC        171
                              Met Glu His Gln Leu Leu Cys Cys
```

-continued

```
                              1              5

GAA GTG GAA ACC ATC CGC CGC GCG TAC CCC GAT GCC AAC CTC CTC AAC      219
Glu Val Glu Thr Ile Arg Arg Ala Tyr Pro Asp Ala Asn Leu Leu Asn
     10                  15                  20

GAC CGG GTG CTG CGG GCC ATG CTG AAG GCG GAG GAG ACC TGC GCG CCC      267
Asp Arg Val Leu Arg Ala Met Leu Lys Ala Glu Glu Thr Cys Ala Pro
 25                  30                  35                  40

TCG GTG TCC TAC TTC AAA TGT GTG CAG AAG GAG GTC CTG CCG TCC ATG      315
Ser Val Ser Tyr Phe Lys Cys Val Gln Lys Glu Val Leu Pro Ser Met
                 45                  50                  55

CGG AAG ATC GTC GCC ACC TGG ATG CTG GAG GTC TGC GAG GAA CAG AAG      363
Arg Lys Ile Val Ala Thr Trp Met Leu Glu Val Cys Glu Glu Gln Lys
             60                  65                  70

TGC GAG GAG GAG GTC TTC CCG CTG GCC ATG AAC TAC CTG GAC CGC TTC      411
Cys Glu Glu Glu Val Phe Pro Leu Ala Met Asn Tyr Leu Asp Arg Phe
         75                  80                  85

CTG TCG CTG GAG CCC GTG AAA AAG AGC CGC CTG CAG CTG CTG GGG GCC      459
Leu Ser Leu Glu Pro Val Lys Lys Ser Arg Leu Gln Leu Leu Gly Ala
     90                  95                 100

ACT TGC ATG TTC GTG GCC TCT AAG ATG AAG GAG ACC ATC CCC CTG ACG      507
Thr Cys Met Phe Val Ala Ser Lys Met Lys Glu Thr Ile Pro Leu Thr
105                 110                 115                 120

GCC GAG AAG CTG TGC ATC TAC ACC GAC AAC TCC ATC CGG CCC GAG GAG      555
Ala Glu Lys Leu Cys Ile Tyr Thr Asp Asn Ser Ile Arg Pro Glu Glu
                125                 130                 135

CTG CTG CAA ATG GAG CTG CTC CTG GTG AAC AAG CTC AAG TGG AAC CTG      603
Leu Leu Gln Met Glu Leu Leu Leu Val Asn Lys Leu Lys Trp Asn Leu
            140                 145                 150

GCC GCA ATG ACC CCG CAC GAT TTC ATT GAA CAC TTC CTC TCC AAA ATG      651
Ala Ala Met Thr Pro His Asp Phe Ile Glu His Phe Leu Ser Lys Met
        155                 160                 165

CCA GAG GCG GAG GAG AAC AAA CAG ATC ATC CGC AAA CAC GCG CAG ACC      699
Pro Glu Ala Glu Glu Asn Lys Gln Ile Ile Arg Lys His Ala Gln Thr
    170                 175                 180

TTC GTT GCC CTC TGT GCC ACA GAT GTG AAG TTC ATT TCC AAT CCG CCC      747
Phe Val Ala Leu Cys Ala Thr Asp Val Lys Phe Ile Ser Asn Pro Pro
185                 190                 195                 200

TCC ATG GTG GCA GCG GGG AGC GTG GTG GCC GCA GTG CAA GGC CTG AAC      795
Ser Met Val Ala Ala Gly Ser Val Val Ala Ala Val Gln Gly Leu Asn
                205                 210                 215

CTG AGG AGC CCC AAC AAC TTC CTG TCC TAC TAC CGC CTC ACA CGC TTC      843
Leu Arg Ser Pro Asn Asn Phe Leu Ser Tyr Tyr Arg Leu Thr Arg Phe
            220                 225                 230

CTC TCC AGA GTG ATC AAG TGT GAC CCA GAC TGC CTC CGG GCC TGC CAG      891
Leu Ser Arg Val Ile Lys Cys Asp Pro Asp Cys Leu Arg Ala Cys Gln
        235                 240                 245

GAG CAG ATC GAA GCC CTG CTG GAG TCA AGC CTG CGC CAG GCC CAG CAG      939
Glu Gln Ile Glu Ala Leu Leu Glu Ser Ser Leu Arg Gln Ala Gln Gln
    250                 255                 260

AAC ATG GAC CCC AAG GCC GCC GAG GAG GAG GAA GAG GAG GAG GAG GAG      987
Asn Met Asp Pro Lys Ala Ala Glu Glu Glu Glu Glu Glu Glu Glu Glu
265                 270                 275                 280

GTG GAC CTG GCT TGC ACA CCC ACC GAC GTG CGG GAC GTG GAC ATC TGA     1035
Val Asp Leu Ala Cys Thr Pro Thr Asp Val Arg Asp Val Asp Ile
                285                 290                 295

GGGCGCCAGG CAGGCGGGCG CCACCGCCAC CCGCAGCGAG GGCGGAGCCG GCCCCAGGTG   1095

CTCCACTGAC AGTCCCTCCT CTCCGGAGCA TTTGATACCC AGAAGGGAAA GCTTCATTCT   1155

CCTTGTTGTT GGTTGTTTTT TCCTTTGCTC TTTCCCCCTT CCATCTCTGA CTTAAGCAAA   1215
```

-continued

```
AGAAAAAGAT TACCCAAAAA CTGTCTTTAA AAGAGAGAGA GAGAAAAAAA AAATAGTATT   1275
TGCATAACCC TGAGCGGTGG GGGAGGAGGG TTGTGCTACA GATGATAGAG GATTTTATAC   1335
CCCAATAATC AACTCGTTTT TATATTAATG TACTTGTTTC TCTGTTGTAA GAATAGGCAT   1395
TAACACAAAG GAGGCGTCTC GGGAGAGGAT TAGGTTCCAT CCTTTACGTG TTTAAAAAAA   1455
AGCATAAAAA CATTTTAAAA ACATAGAAAA ATTCAGCAAA CCATTTTTAA AGTAGAAGAG   1515
GGTTTTAGGT AGAAAAACAT ATTCTTGTGC TTTTCCTGAT AAAGCACAGC TGTAGTGGGG   1575
TTCTAGGCAT CTCTGTACTT TGCTTGCTCA TATGCATGTA GTCACTTTAT AAGTCATTGT   1635
ATGTTATTAT ATTCCGTAGG TAGATGTGTA ACCTCTTCAC CTTATTCATG GCTGAAGTCA   1695
CCTCTTGGTT ACAGTAGCGT AGCGTGGCCG TGTGCATGTC CTTTGCGCCT GTGACCACCA   1755
CCCCAACAAA CCATCCAGTG ACAAACCATC CAGTGGAGGT TTGTCGGGCA CCAGCCAGCG   1815
TAGCAGGGTC GGGAAAGGCC ACCTGTCCCA CTCCTACGAT ACGCTACTAT AAAGAGAAGA   1875
CGAAATAGTG ACATAATATA TTCTATTTTT ATACTCTTCC TATTTTTGTA GTGACCTGTT   1935
TATGAGATGC TGGTTTTCTA CCCAACGGCC CTGCAGCCAG CTCACGTCCA GGTTCAACCC   1995
ACAGCTACTT GGTTTGTGTT CTTCTTCATA TTCTAAAACC ATTCCATTTC CAAGCACTTT   2055
CAGTCCAATA GGTGTAGGAA ATAGCGCTGT TTTTGTTGTG TGTGCAGGGA GGGCAGTTTT   2115
CTAATGGAAT GGTTTGGGAA TATCCATGTA CTTGTTTGCA AGCAGGACTT TGAGGCAAGT   2175
GTGGGCCACT GTGGTGGCAG TGGAGGTGGG GTGTTTGGGA GGCTGCGTGC CAGTCAAGAA   2235
GAAAAAGGTT TGCATTCTCA CATTGCCAGG ATGATAAGTT CCTTTCCTTT TCTTTAAAGA   2295
AGTTGAAGTT TAGGAATCCT TTGGTGCCAA CTGGTGTTTG AAAGTAGGGA CCTCAGAGGT   2355
TTACCTAGAG AACAGGTGGT TTTTAAGGGT TATCTTAGAT GTTTCACACC GGAAGGTTTT   2415
TAAACACTAA AATATATAAT TTATAGTTAA GGCTAAAAAG TATATTTATT GCAGAGGATG   2475
TTCATAAGGC CAGTATGATT TATAAATGCA ATCTCCCCTT GATTTAAACA CACAGATACA   2535
CACACACACA CACACACACA CACAAACCTT CTGCCTTTGA TGTTACAGAT TTAATACAGT   2595
TTATTTTTAA AGATAGATCC TTTTATAGGT GAGAAAAAAA CAATCTGGAA GAAAAAAACC   2655
ACACAAAGAC ATTGATTCAG CCTGTTTGGC GTTTCCCAGA GTCATCTGAT TGGACAGGCA   2715
TGGGTGCAAG GAAAATTAGG GTACTCAACC TAAGTTCGGT TCCGATGAAT TCTTATCCCC   2775
TGCCCCTTCC TTTAAAAAAC TTAGTGACAA AATAGACAAT TTGCACATCT TGGCTATGTA   2835
ATTCTTGTAA TTTTTATTTA GGAAGTGTTG AAGGGAGGTG GCAAGAGTGT GGAGGCTGAC   2895
GTGTGAGGGA GGACAGGCGG GAGGAGGTGT GAGGAGGAGG CTCCCGAGGG GAAGGGGCGG   2955
TGCCCACACC GGGGACAGGC CGCAGCTCCA TTTTCTTATT GCGCTGCTAC CGTTGACTTC   3015
CAGGCACGGT TTGGAAATAT TCACATCGCT TCTGTGTATC TCTTTCACAT TGTTTGCTGC   3075
TATTGGAGGA TCAGTTTTTT GTTTTACAAT GTCATATACT GCCATGTACT AGTTTTAGTT   3135
TTCTCTTAGA ACATTGTATT ACAGATGCCT TTTTTGTAGT TTTTTTTTTT TTTATGTGAT   3195
CAATTTTGAC TTAATGTGAT TACTGCTCTA TTCCAAAAAG GTTGCTGTTT CACAATACCT   3255
CATGCTTCAC TTAGCCATGG TGGACCCAGC GGGCAGGTTC TGCCTGCTTT GGCGGGCAGA   3315
CACGCGGGCG CGATCCCACA CAGGCTGGCG GGGGCCGGCC CCGAGGCCGC GTGCGTGAGA   3375
ACCGCGCCGG TGTCCCCAGA GACCAGGCTG TGTCCCTCTT CTCTTCCCTG CGCCTGTGAT   3435
GCTGGGCACT TCATCTGATC GGGGGCGTAG CATCATAGTA GTTTTTACAG CTGTGTTATW   3495
CTTTGCGTGT AGCTATGGAA GTTGCATAAT TATTATTATT ATTATTATAA CAAGTGTGTC   3555
```

-continued

```
TTACGTGCCA CCACGGCGTT GTACCTGTAG GACTCTCATT CGGGATGATT GGAATAGCTT   3615

CTGGAATTTG TTCAAGTTTT GGGTATGTTT AATCTGTTAT GTACTAGTGT TCTGTTTGTT   3675

ATTGTTTTGT TAATTACACC ATAATGCTAA TTTAAAGAGA CTCCAAATCT CAATGAAGCC   3735

AGCTCACAGT GCTGTGTGCC CCGGTCACCT AGCAAGCTGC CGAACCAAAA GAATTTGCAC   3795

CCCGCTGCGG GCCCACGTGG TTGGGGCCCT GCCCTGGCAG GGTCATCCTG TGCTCGGAGG   3855

CCATCTCGGG CACAGGCCCA CCCCGCCCCA CCCCTCCAGA ACACGGCTCA CGCTTACCTC   3915

AACCATCCTG GCTGCGGCGT CTGTCTGAAC CACGCGGGGG CCTTGAGGGA CGCTTTGTCT   3975

GTCGTGATGG GGCAAGGGCA CAAGTCCTGG ATGTTGTGTG TRTCGAGAGG CCAAAGGCTG   4035

GTGGCAAGTG CACGGGGCAC AGCGGAGTCT GTCCTGTGAC GCGCAAGTCT GAGGGTCTGG   4095

GCGGCGGGCG GCTGGGTCTG TGCATTTCTG GTTGCACCGC GGCGCTTCCC AGCACCAACA   4155

TGTAACCGGC ATGTTTCCAG CAGAAGACAA AAAGACAAAC ATGAAAGTCT AGAAATAAAA   4215

CTGGTAAAAC CCCAAAAAAA AAAAAAAAA                                     4244
```

(2) INFORMATION FOR SEQ ID NO:2:

(i) SEQUENCE CHARACTERISTICS:
(A) LENGTH: 295 amino acids
(B) TYPE: amino acid
(D) TOPOLOGY: linear (ii) MOLECULE TYPE: protein (xi) SEQUENCE DESCRIPTION: SEQ ID NO:2:

```
Met Glu His Gln Leu Leu Cys Cys Glu Val Glu Thr Ile Arg Arg Ala
  1               5                  10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Glu Val Phe Pro Leu
 65                  70                  75                  80

Ala Met Asn Tyr Leu Asp Arg Phe Leu Ser Leu Glu Pro Val Lys Lys
                 85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
```

-continued

```
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295
```

(2) INFORMATION FOR SEQ ID NO:3:

(i) SEQUENCE CHARACTERISTICS:
(A) LENGTH: 150 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:3:

```
Met Arg Ala Ile Leu Val Asp Trp Leu Val Glu Val Gly Glu Glu Tyr
1               5                   10                  15

Lys Leu Gln Asn Glu Thr Leu His Leu Ala Val Asn Tyr Ile Asp Arg
            20                  25                  30

Phe Leu Ser Ser Met Ser Val Leu Arg Gly Lys Leu Gln Leu Val Gly
        35                  40                  45

Thr Ala Ala Met Leu Leu Ala Ser Lys Phe Glu Glu Ile Tyr Pro Pro
    50                  55                  60

Glu Val Ala Glu Phe Val Tyr Ile Thr Asp Asp Thr Tyr Thr Lys Lys
65                  70                  75                  80

Gln Val Leu Arg Met Glu His Leu Val Leu Lys Val Leu Thr Phe Asp
                85                  90                  95

Leu Ala Ala Pro Thr Val Asn Gln Phe Leu Thr Gln Tyr Phe Leu His
            100                 105                 110

Gln Gln Pro Ala Asn Cys Lys Val Glu Ser Leu Ala Met Phe Leu Gly
        115                 120                 125

Glu Leu Ser Leu Ile Asp Ala Asp Pro Tyr Leu Lys Tyr Leu Pro Ser
    130                 135                 140

Val Ile Ala Gly Ala Ala
145                 150
```

(2) INFORMATION FOR SEQ ID NO:4:

(i) SEQUENCE CHARACTERISTICS:
(A) LENGTH: 152 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:4:

```
Met Arg Lys Ile Val Ala Thr Trp Met Leu Glu Val Cys Glu Glu Gln
1               5                   10                  15

Lys Cys Glu Glu Glu Val Phe Pro Leu Ala Met Asn Tyr Leu Asp Arg
            20                  25                  30

Phe Leu Ser Leu Glu Pro Val Lys Lys Ser Arg Leu Gln Leu Leu Gly
        35                  40                  45
```

-continued

```
Ala Thr Cys Met Phe Val Ala Ser Lys Met Lys Glu Thr Ile Pro Leu
    50                  55                  60

Thr Ala Glu Lys Leu Cys Ile Tyr Thr Asp Asn Ser Ile Arg Pro Glu
65                  70                  75                  80

Glu Leu Leu Gln Met Glu Leu Leu Leu Val Asn Lys Leu Lys Trp Asn
                85                  90                  95

Leu Ala Ala Met Thr Pro His Asp Phe Ile Glu His Phe Leu Ser Lys
            100                 105                 110

Met Pro Glu Ala Glu Glu Asn Lys Gln Ile Ile Arg Lys His Ala Gln
        115                 120                 125

Thr Phe Val Ala Leu Cys Ala Thr Asp Val Lys Phe Ile Ser Asn Pro
    130                 135                 140

Pro Ser Met Val Ala Ala Gly Ser
145                 150
```

(2) INFORMATION FOR SEQ ID NO:5:

(i) SEQUENCE CHARACTERISTICS:
(A) LENGTH: 149 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:5:

```
Met Arg Cys Ile Leu Val Asp Trp Leu Val Glu Val Ser Glu Glu Asp
1               5                   10                  15

Lys Leu His Arg Glu Thr Leu Phe Leu Gly Val Asn Tyr Ile Asp Arg
            20                  25                  30

Phe Leu Ser Lys Ile Ser Val Leu Arg Gly Lys Leu Gln Leu Val Gly
        35                  40                  45

Ala Ala Ser Met Phe Leu Ala Ala Lys Tyr Glu Glu Ile Tyr Pro Pro
    50                  55                  60

Asp Val Lys Glu Phe Ala Tyr Ile Thr Asp Asp Thr Tyr Thr Ser Gln
65                  70                  75                  80

Gln Val Leu Arg Met Glu His Leu Ile Leu Lys Val Leu Thr Phe Asp
                85                  90                  95

Val Ala Val Pro Thr Thr Asn Trp Phe Cys Glu Asp Phe Leu Lys Ser
            100                 105                 110

Cys Asp Ala Asp Asp Lys Leu Lys Ser Leu Thr Met Phe Leu Thr Glu
        115                 120                 125

Leu Thr Leu Ile Asp Met Asp Ala Tyr Leu Lys Tyr Leu Pro Ser Ile
    130                 135                 140

Thr Ala Ala Ala Ala
145
```

(2) INFORMATION FOR SEQ ID NO:6:

(i) SEQUENCE CHARACTERISTICS:
(A) LENGTH: 148 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:6:

```
Met Arg Ala Ile Leu Ile Asp Trp Leu Val Gln Val Gln Met Lys Phe
1               5                   10                  15
```

-continued

```
Arg Leu Leu Gln Glu Thr Met Tyr Met Thr Val Ser Ile Ile Asp Arg
            20                  25                  30

Phe Met Gln Asn Asn Cys Val Pro Lys Lys Met Leu Gln Leu Val Gly
        35                  40                  45

Val Thr Ala Met Phe Ile Ala Ser Lys Tyr Glu Glu Met Tyr Pro Pro
    50                  55                  60

Glu Ile Gly Asp Phe Ala Phe Val Thr Asp Asn Thr Tyr Thr Lys His
65                  70                  75                  80

Gln Ile Arg Gln Met Glu Met Lys Ile Leu Arg Ala Leu Asn Phe Gly
                85                  90                  95

Leu Gly Arg Pro Leu Pro Leu His Phe Leu Arg Arg Ala Ser Lys Ile
            100                 105                 110

Gly Glu Val Asp Val Glu Gln His Thr Leu Ala Lys Tyr Leu Met Glu
        115                 120                 125

Leu Thr Met Leu Asp Tyr Asp Met Val His Phe Pro Pro Ser Gln Ile
    130                 135                 140

Ala Ala Gly Ala
145
```

(2) INFORMATION FOR SEQ ID NO:7:

(i) SEQUENCE CHARACTERISTICS:
(A) LENGTH: 148 amino acids
(B) TYPE: amino acid
(C) STRANDEDNESS: Not Relevant
(D) TOPOLOGY: linear (ii) MOLECULE TYPE: peptide (vi) ORIGINAL SOURCE:
(A) ORGANISM: S. pombe (xi) SEQUENCE DESCRIPTION: SEQ ID NO:7:

```
Met Arg Gly Ile Leu Thr Asp Trp Leu Ile Glu Val His Ser Arg Phe
1               5                   10                  15

Arg Leu Leu Pro Glu Thr Leu Phe Leu Ala Val Asn Ile Ile Asp Arg
            20                  25                  30

Phe Leu Ser Leu Arg Val Cys Ser Leu Asn Lys Leu Gln Leu Val Gly
        35                  40                  45

Ile Ala Ala Leu Phe Ile Ala Ser Lys Tyr Glu Glu Val Met Cys Pro
    50                  55                  60

Ser Val Gln Asn Phe Val Tyr Met Ala Asp Gly Gly Tyr Asp Glu Glu
65                  70                  75                  80

Glu Ile Leu Gln Ala Glu Arg Tyr Ile Leu Arg Val Leu Glu Phe Asn
                85                  90                  95

Leu Ala Tyr Pro Asn Pro Met Asn Phe Leu Arg Arg Ile Ser Lys Ala
            100                 105                 110

Asp Phe Tyr Asp Ile Gln Thr Arg Thr Val Ala Lys Tyr Leu Val Glu
        115                 120                 125

Ile Gly Leu Leu Asp His Lys Leu Leu Pro Tyr Pro Pro Ser Gln Gln
    130                 135                 140

Cys Ala Ala Ala
145
```

(2) INFORMATION FOR SEQ ID NO:8:

(i) SEQUENCE CHARACTERISTICS:
(A) LENGTH: 152 amino acids

-continued

```
         (B) TYPE: amino acid
         (C) STRANDEDNESS: Not Relevant
         (D) TOPOLOGY: linear

    (ii) MOLECULE TYPE: peptide

    (vi) ORIGINAL SOURCE:
         (A) ORGANISM: S. cerevisiae

    (xi) SEQUENCE DESCRIPTION: SEQ ID NO:8:

Met Arg Phe Leu Ile Phe Asp Phe Ile Met Tyr Cys His Thr Arg Leu
1               5                   10                  15

Asn Leu Ser Thr Ser Thr Leu Phe Leu Thr Phe Thr Ile Leu Asp Lys
            20                  25                  30

Tyr Ser Ser Arg Phe Ile Ile Lys Ser Tyr Asn Tyr Gln Leu Leu Ser
        35                  40                  45

Leu Thr Ala Leu Trp Ile Ser Ser Lys Phe Trp Asp Ser Lys Asn Arg
    50                  55                  60

Met Ala Thr Leu Lys Val Leu Gln Asn Leu Cys Cys Asn Gln Tyr Ser
65                  70                  75                  80

Ile Lys Gln Phe Thr Thr Met Glu Met His Leu Phe Lys Ser Leu Asp
                85                  90                  95

Trp Ser Ile Cys Gln Ser Ala Thr Phe Asp Ser Tyr Ile Asp Ile Phe
            100                 105                 110

Leu Phe Gln Ser Thr Ser Pro Leu Ser Pro Gly Val Val Leu Ser Ala
        115                 120                 125

Pro Leu Glu Ala Phe Ile Gln Gln Lys Leu Ala Leu Leu Asn Asn Ala
    130                 135                 140

Ala Gly Thr Ala Ile Asn Lys Ser
145                 150
```

PRAD1 TRANSGENIC MICE

This application is a division of application Ser. No. 07/667,711, filed Mar. 11, 1991, (status: pending).

BACKGROUND OF THE INVENTION

Partial funding for the work described herein was provided by the U.S. Government, which has certain rights in the invention.

This invention relates to the field of cyclins.

The cyclins are a class of eukaryotic proteins that were originally identified by their cyclic accumulation and destruction at defined points in embryonic cell cycles (Evans et al., Cell 33:389–396, 1983). They bind to and are essential for activation of cdc2 protein kinase (reviewed in Murray et al., Science 246:614–621, 1989; Nurse, Nature 344:503–508, 1990; Draetta et al., Cell 56:829–838, 1989). At present, the cyclins can be divided into three families on the basis of their kinetics of oscillation across the cell cycle, their amino acid sequences, and, in some cases, genetic experiments in yeast that determine when their functions are needed (reviewed in Nurse, 1990; Nasmyth, Cell 63:1117–1120, 1990; Westendorf, J. Cell Biol. 108:1431–1444, 1989). The B-type "mitotic" cyclins drive cells into mitosis; their sequences are conserved from yeast to human (Nurse, 1990; Westendorf et al., 1989; and Pines et al., Cell 58:833–846, 1989). The A-type cyclins, which are less well understood, may act earlier in the cell cycle (Minshull et al., EMBO J. 9:2865–2875, 1990; Pines et al., Nature 346:760–763, 1990; Swenson et al., Cell 47:861–870, 1986). The recently described CLNs (or "G1 cyclins") of budding yeast are thought to perform analogous functions by interacting with cdc2 homologues at START, driving cells into S-phase (Nasmyth, 1990). A, B, and CLN cyclins may act as stage-specific regulators of progress across the cell cycle by conferring selective substrate specificity upon cdc2 kinase (Minshull et al., 1990) or by selectively targeting cdc2 to different intracellular compartments.

SUMMARY OF THE INVENTION

The invention features a novel cyclin, prad1, and an isolated DNA (termed PRAD1) which encodes it. This DNA may be single-stranded or double-stranded, and may be genomic DNA, CDNA, or synthetic DNA. It may be identical to a naturally-occurring PRAD1 sequence (such as human PRAD1 cDNA, SEQ ID NO:1) or may differ from such sequence by the deletion, addition, or substitution of one or more nucleotides. By "isolated" is meant that the DNA is free of the coding sequences of genes that, in the naturally-occurring genome of the organism from which the DNA of the invention is derived, immediately flank the gene encoding prad1. Included within the term prad1 is human prad1 and any homolog of human prad1 (i.e., from another animal species, or a genetically altered version of a naturally-occurring prad1 which exhibits a biological activity similar to that of the naturally-occurring protein) encoded by a DNA which is capable of hybridizing (1) under stringent hybridization conditions (Sambrook et al., Molecular Cloning: A Laboratory Manual, 2nd edn., Cold Spring Harbor, N.Y., 1989: herein incorporated by reference) to a single-stranded probe consisting of a segment of at least eight (preferably 18–40) nucleotides of human PRAD1 cDNA (SEQ ID NO:1) or human PRAD1 genomic DNA, or (2) under less stringent conditions (e.g., washing at 2×SSC, at 40° C.) to a probe consisting of a segment of at least 40 (preferably 200–5000) nucleotides of human PRAD1 cDNA (SEQ ID NO:1) or human PRAD1 genomic DNA. Also within the invention are peptide fragments of a naturally-occurring prad1, which fragments are at least six amino acids in length and preferably 10–50 amino acids; and single-stranded DNA or RNA probes (preferably radioactively labelled) containing at least 8 nucleotides of, but less than all of, human PRAD1-encoding RNA, human PRAD1 cDNA (SEQ ID NO:1) or human PRAD1 genomic DNA, and preferably between 10 and 5000 bases. Such DNA or RNA probes may be used in a diagnostic method which includes the steps of obtaining a nucleic acid sample from an animal suspected of having a given neoplastic condition (or from a known tumor); contacting the nucleic acid sample with a single-stranded DNA or RNA probe capable of hybridizing to the PRAD1 homolog of the species to which the animal belongs; and detecting the level of hybridization of the probe with the nucleic acid sample, such level being diagnostic for the neoplastic condition. Two examples of neoplastic conditions that may be diagnosed by this method include centrocytic lymphomas, which appear to express abnormally high levels of PRAD1 mRNA, and those breast cancers which are characterized by a high degree of amplification of PRAD1 DNA.

The DNA sequence of the invention, which may be under the transcriptional control of a heterologous promoter (defined as a promoter sequence other than the naturally-occurring promoter of the gene encoding prad1), may be incorporated into a vector (such as a phage) and thereby introduced into a cell. Included within the invention is a eukarydtic or prokaryotic cell (or an essentially homogeneous population of such cells) containing (and preferably capable of expressing) a recombinant DNA molecule encoding prad1: that is, a cell into which (or into an ancestor of which) has been introduced, by means of genetic engineering, a DNA molecule encoding prad1, resulting in that DNA molecule's being positioned adjacent to a DNA sequence to which it is not naturally adjacent (e.g., the prad1-encoding sequence is integrated into the genome of such cell). The prad1 protein of the invention may be produced by culturing such cells and recovering prad1 from the cells, or from their medium. Alternatively, DNA or mRNA encoding prad1 may be combined with a standard in vitro expression system to produce prado. Prad1 so produced can be utilized in combination with a pharmacologically-acceptable carrier to promote wound healing in an animal, or can be used to promote proliferation of an animal cell by treating the cell with a proliferation-inducing amount of the protein of the invention (for example, by transfecting the cell with DNA encoding prad1 so that the cell itself produces such a proliferation-inducing amount of prad1). Alternatively, the prad1 (or an antigenic fragment thereof, determined by standard methodology) can be used to raise polyclonal or monoclonal antibodies capable of forming immune complexes with prad1, and thus useful as a diagnostic for certain neoplastic conditions characterized by abnormally high levels of prad1 expression. The method of using such an antibody as a diagnostic would include the steps of obtaining a sample of a tissue of an animal suspected of having a such a neoplastic condition (e.g., certain lymphomas or breast cancers); contacting the sample with the antibody; and detecting the level of immune complexes formed by the antibody, such level being diagnostic for the neoplastic condition.

Also within the invention is a transgenic non-human vertebrate animal (preferably a mammal such as a rodent, e.g., a mouse) bearing a transgene (i.e., a piece of DNA which is artificially inserted into an embryonic cell, and becomes a part of the genome of the animal which develops from that cell) which includes a DNA sequence encoding prad1, and any cells or cell lines derived from such an animal. A transgenic animal is an animal having cells that contain a transgene, which transgene was introduced into the animal, or an ancestor of the animal, at an embryonic stage. If the embryonic stage is a single-cell stage, then all nucleated cells of the animal will carry the transgene. The particular prad1 encoded by the transgene may be endogenous to the species of the transgenic animal, or may be that of a different species (e.g., human). By using a PRAD1 together with an appropriate promoter, a transgenic animal which readily develops neoplasias in a selected organ or tissue type will result, making such animal useful as a model for studying cancer in that organ or tissue.

Other features and advantages of the invention will be apparent from the following detailed description, and from the claims.

DETAILED DESCRIPTION

The drawings are first described.

Drawings

FIG. 1 is a Southern blot of Msp1-digested DNA probed with the 5' PTH gene probe (lanes 1, 2) and 3' PTH gene probe (lanes 3, 4).

FIGS. 2A–B is a diagrammatic representation of (a) the normal PTH gene, and (b) the two fragments resulting from the rearrangement in tumor M.

FIG. 6 is a representation of the nucleotide sequence and predicted amino acid sequence of human PRAD1 (SEQ ID NO:1) cDNA.

FIG. 7 is an illustration of sequence homology between the "cyclin box" region of human prad1 and the corresponding regions of some A-type, B-type, and G1 cyclins.

Figure 9A:
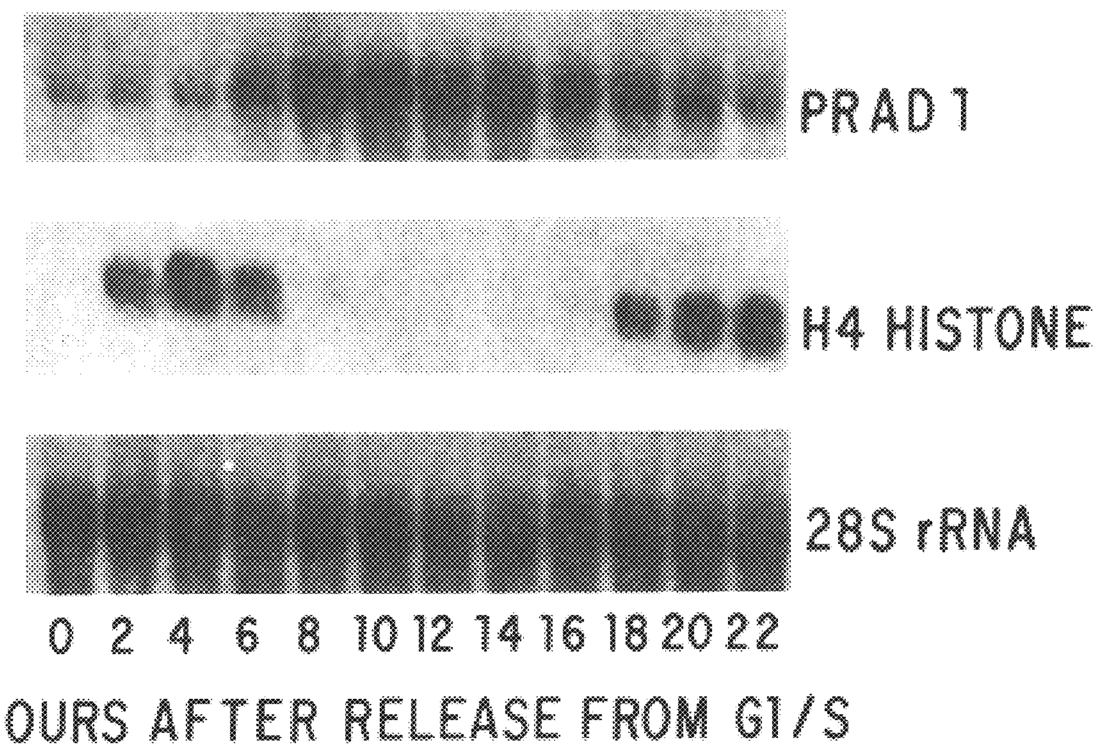
Figure 9B:
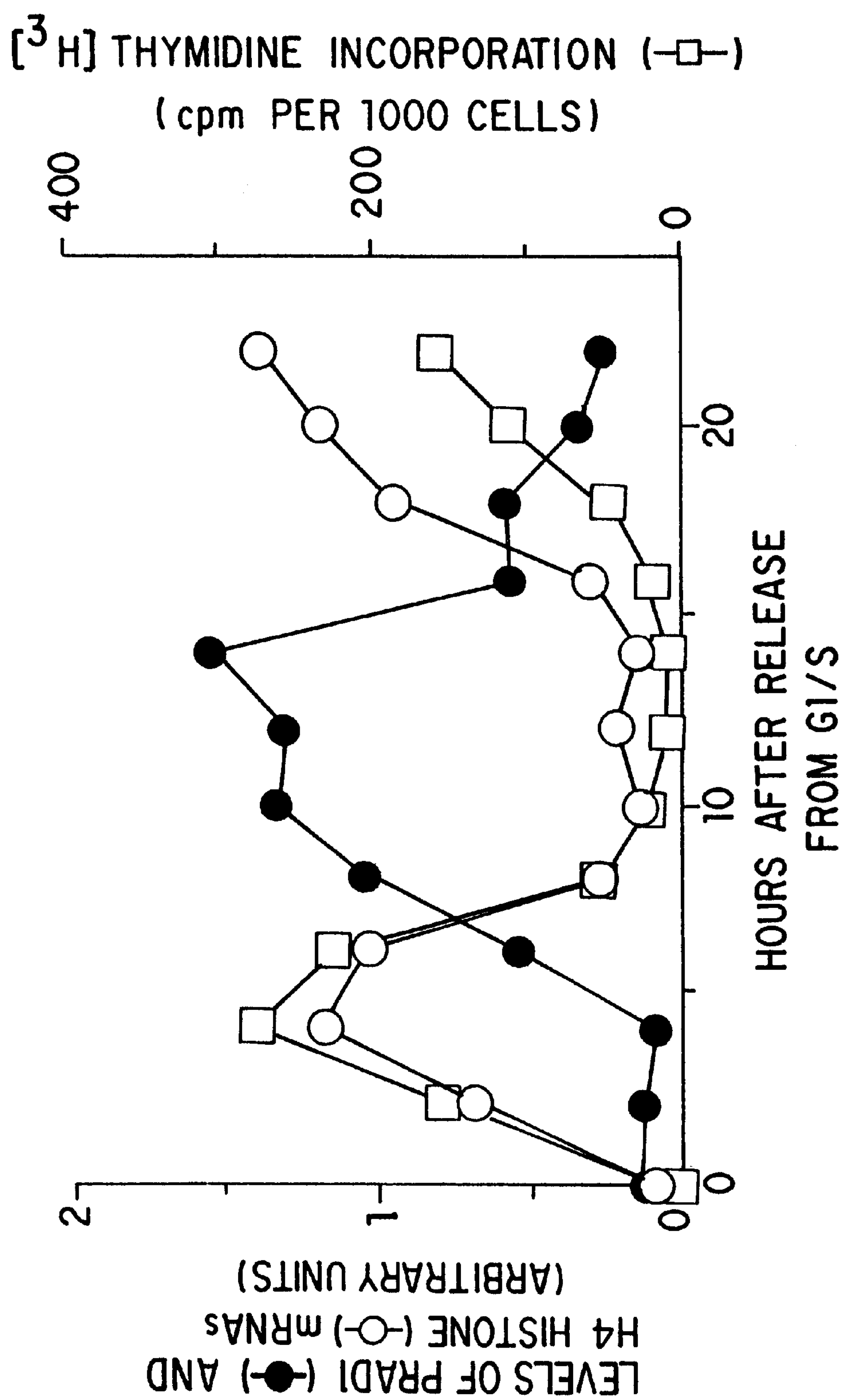
Figure 10A:
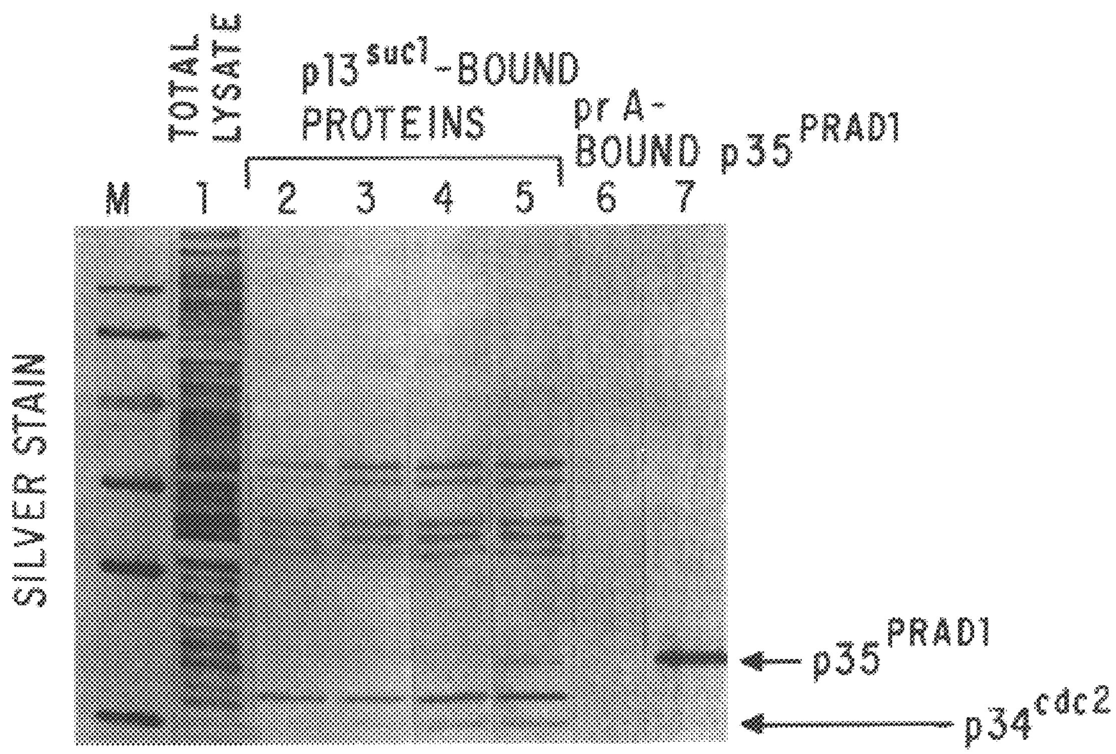
Figure 10B:
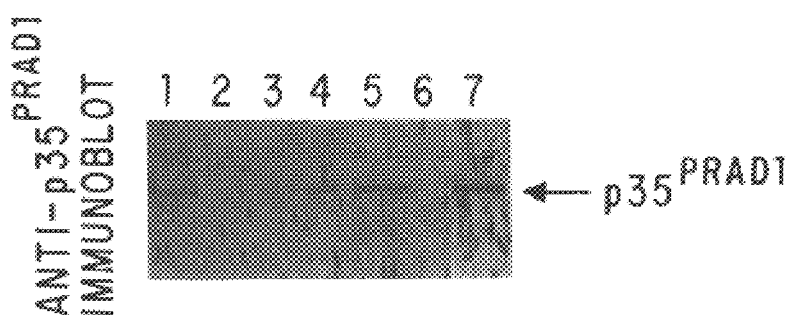
Figure 10C:
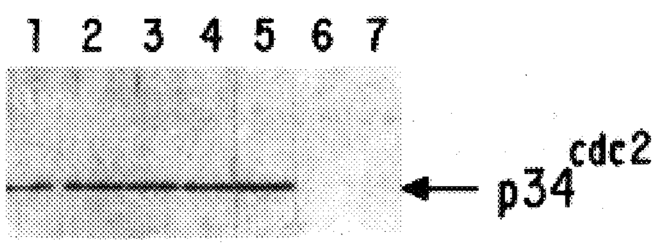
Figure 10D:
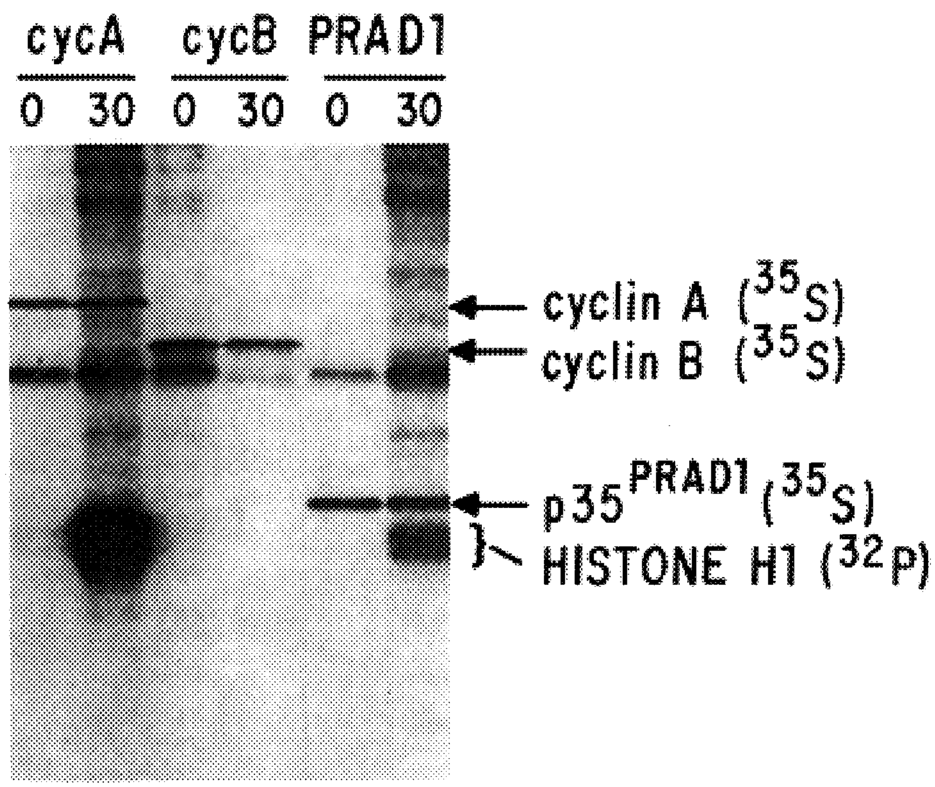

FIGS. 9A–B is (a) a Northern blot analysis of HeLa cell RNA probed with a human PRAD1 cDNA (SEQ ID NO:1) probe, an H4 histone probe, and 28S rRNA; and (b) a graph depicting the results of the Northern blot.

FIGS. 10A–D is an analysis of the biological activity of recombinant human prad1.

IDENTIFICATION OF HUMAN PRAD1

Previous studies on DNA from cells of a benign parathyroid adenoma (reported in Arnold et al., J. Clin. Invest. 83:2034–2040, 1989) revealed evidence of a DNA rearrangement involving the parathyroid hormone (PTH) chromosomal locus (at chromosome 11, band p15) and a segment of DNA (identified as Human Genome Database assignment D11S287) which normally maps to chromosome 11, band q13. It is now known that (a) although a number of previously-identified oncogenes (including INT-2 and HST-1), as well as the translocation breakpoint marker BCL-1 and possibly the gene for multiple endocrine neoplasia type I (MEN-I), map to the 11q13 region, the so-called D11S287 locus rearranged in at least some parathyroid adenomas is distinct from these previously-described markers; (b) D11S287 mRNA, while detectable in all tissues analyzed, is significantly overexpressed in those parathyroid adenomas which have a 11q13/11p15 chromosomal rearrangement, and also in certain lymphomas (notably centrocytic lymphomas) characterized by rearrangement of the BCL-1 locus; and (c) the D11S287 locus is amplified and expressed in many squamous cell and mammary carcinomas. This evidence suggests that D11S287 (also referred to herein as human PRAD1, for parathyroid adenoma) is a newly-identified oncogene which figures in a variety of types of neoplasms.

Cloning Human PRAD1 CDNA (SEO ID NO:1)

Human PRAD1 cDNA (SEQ ID NO: 1) has been cloned and sequenced by the methods described in detail below, yielding the sequence shown in FIG. 6. The longest open reading frame, starting at the first ATG codon, encodes a predicted protein of 295 amino acids ($M_r$ 33,729). Screening the Genbank peptide database with this sequence reveals significant homology only to members of the cyclin family, with greatest similarity in the region conserved among cyclins, ranging from 19.1% to 33.6% identity, and 44.1% to 59.2% similarity. The human PRAD1 (SEQ ID NO:1) protein (prad1) has significant sequence similarities to all three types of cyclins (A, B, and CLN cyclins), but cannot readily be assigned to any one type. This suggests that prad1 may represent a new and different cyclin family member.

PRAD1 Expression

PRAD1 mRNA is expressed in many tissues and is highly conserved across species (FIG. 7). As with other cyclin mRNAs expressed in human cells (Pines et al., Cell 58:833–846, 1989; Pines et al., Nature 346:760–763, 1990), human PRAD1 mRNA levels vary across the cell cycle (FIG. 9), consistent with but not proving a role in cell cycle regulation. The peak in PRAD1 mRNA levels occurs late in the cell cycle or in G1.

Biological Activity of Recombinant Human Prad1 Protein

Bacterially expressed recombinant human prad1, produced as described in detail below, was used to further investigate the link between human PRAD1 and the cyclins. Cyclins are known to form complexes with $p34^{cdc2}$ protein kinase, leading to its activation which can be assayed using exogenous histone H1 as a substrate. In addition, cyclin/$p34^{cdc2}$ complexes can be purified by exploiting the ability of beads linked to $p13^{suc1}$, another cell cycle protein, to avidly bind $p34^{cdc2}$ and, in turn, co-purify any proteins complexed with $p34^{cdc2}$ (Draetta et al., Cell 56:829–838, 1989). When recombinant human prad1 was added to clam embryo interphase cell lysates (which lack endogenous cyclins and contain inactive $p34^{cdc2}$), both $p_{34}{}^{cdc2}$ and prad1 were bound by $p13^{suc1}$-beads (FIG. 10) As prad1 does not bind to protein A-Sepharaose beads, its binding to $p13^{suc1}$-beads is most likely due to its interaction with $p34^{cdc2}$ or a closely related protein. Furthermore, kinase activity was induced by the addition of the human PRAD1 (SEQ ID NO:1) in vitro translation product to interphase lysates (FIG. 10). This kinase activity was lower than that seen with cyclin A. Cyclin B provided a negative control; for reasons not yet understood, our cyclin B translation product was not capable of activating $p_{34}{}^{cdc2}$ in this type of assay. The difference between the activities induced by cyclin A and human prad1 may be specific to this clam assay system, or may reflect a genuine difference between the functions of, or the substrate specificities conferred by, cyclin A vs. human prad1.

Use

Both prad1 and a nucleotide encoding prad1 are useful for the preparation of diagnostic tools for the classification and/or prognosis of lymphomas, breast cancers, and squamous cell cancers, as well as other cancers characterized by a high level of expression and/or amplification of the PRAD1 gene. For example, prad1 or an antigenic peptide fragment of prad1 could be used in accordance with standard methods (see, e.g., Harlow et al., Antibodies: A Laboratory Manual, Cold Spring Harbor Laboratory, Cold Spring Harbor, N.Y., 1988; Yanaihara et al., U.S. Pat. No. 4,855,406; and Slamon et al., U.S. Pat. No. 4,918,162; all of which are herein incorporated by reference) to raise polyclonal or monoclonal antibodies capable of forming immune complexes with prad1, and useful for detecting abnormally high levels of prad1 in a given tissue sample. Similarly, a hybridization probe prepared from a segment of at least 12 (and preferably greater than 250) nucleotides of human PRAD1-encoding RNA, human PRAD1 cDNA (SEQ ID NO:1) or human PRAD1 genomic DNA may be employed as a means for determining the number of copies of PRAD1 present in the genomic DNA of a given sample, or the level of PRAD1 mRNA expressed in cells of such sample.

The nucleic acids of the invention may also be used therapeutically. Oligonucleotides which are antisense to human PRAD1 mRNA (or which express RNA that is antisense to human PRAD1 mRNA) may be synthesized to serve as an anticancer therapy in those cases diagnosed as having a rearrangement or amplification of human PRAD1: such oligonucleotides would be introduced into tumor cells in vivo as a means to reduce production of prad1 in such cells, and thereby to reduce neoplastic growth induced by an overabundance of prad1. (See, for example, Weinberg et al., U.S. Pat. No. 4,740,463, herein incorporated by reference.) By linking a PRAD1 sequence to a selected tissue-specific promoter or enhancer and introducing by standard methods (e.g., as described by Leder et al., U.S. Pat. No. 4,736,866, herein incorporated by reference) the resultant hybrid gene into an animal embryo at an early developmental stage (e.g., the fertilized oocyte stage), a transgenic animal which expresses elevated levels of prad1 in the selected tissue (e.g., breast, squamous cell, B-lymphoid cell, parathyroid, and others) can be produced. The form of PRAD1 utilized can be one which encodes a prad1 similar to that of the animal species used, or it can encode the prad1 homolog of a different species (e.g., human). Such an animal would be useful as an in vivo model for neoplastic disease in the selected tissue. In addition, cells derived from such a transgenic animal may be used to establish an immortal cell line that retains at least some of its differentiated characteristics while proliferating indefinitely in vitro. Alternatively, one could stably transfect primary cells (e.g., a type that has proven difficult to maintain in culture, such as pituitary cells) with a PRAD1 gene linked to an appropriate promoter (e.g., the metallothionin promoter) which ensures high levels of expression of the gene, and thereby establish an immortal cell line derived from such primary cells. PRAD1 sequences may be particularly useful in this regard because overexpression of PRAD1 (at least in parathyroid tissues) appears to trigger the proliferation of normally quiescent cells without causing them to completely lose their differentiated phenotype.

EXPERIMENTAL DATA

Figure 1:
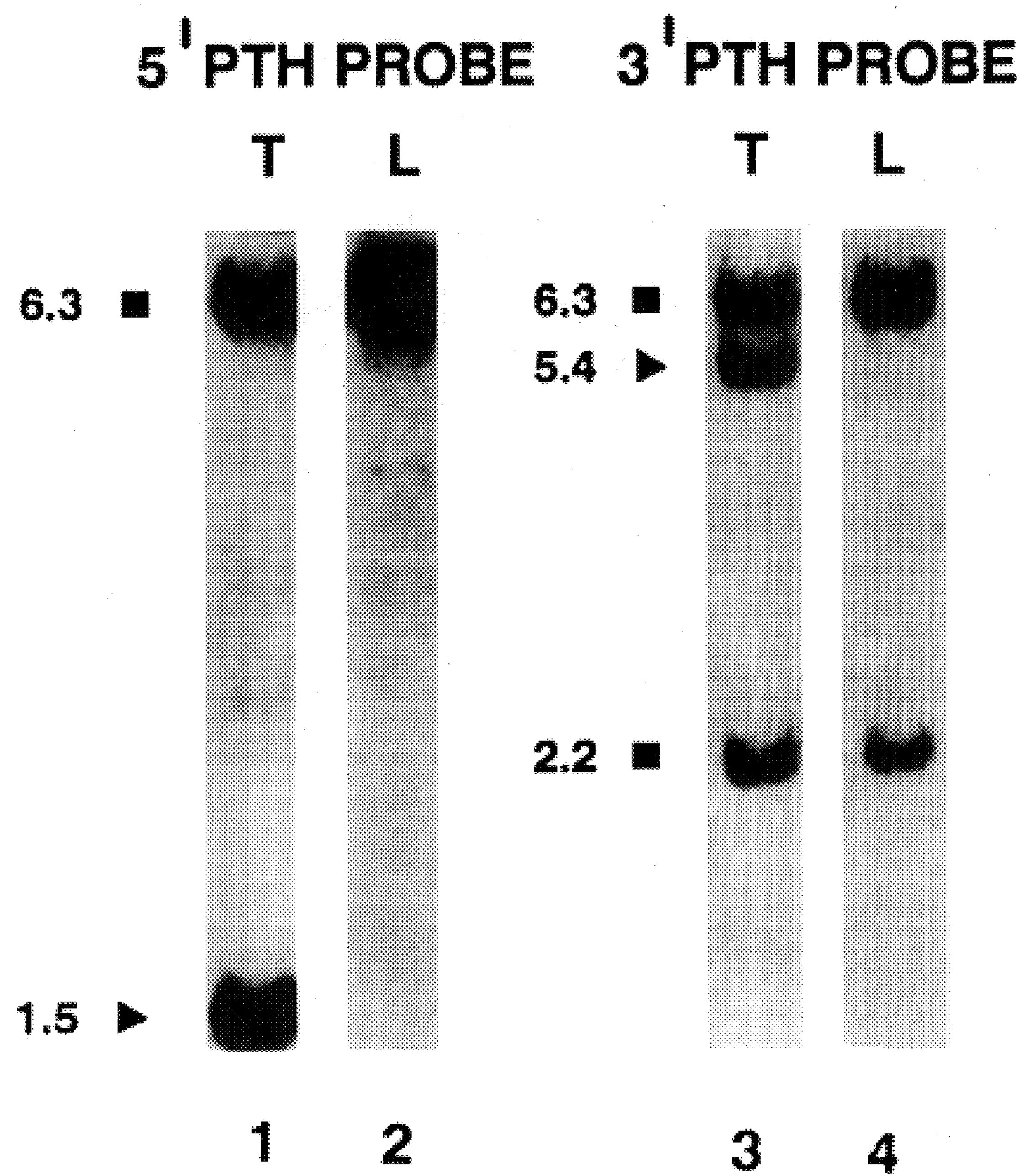
Figure 2A:
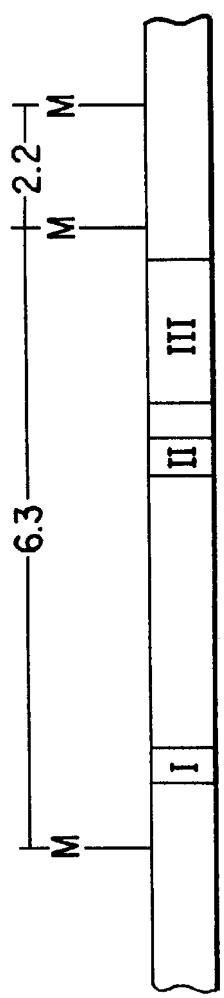
Figure 2B:
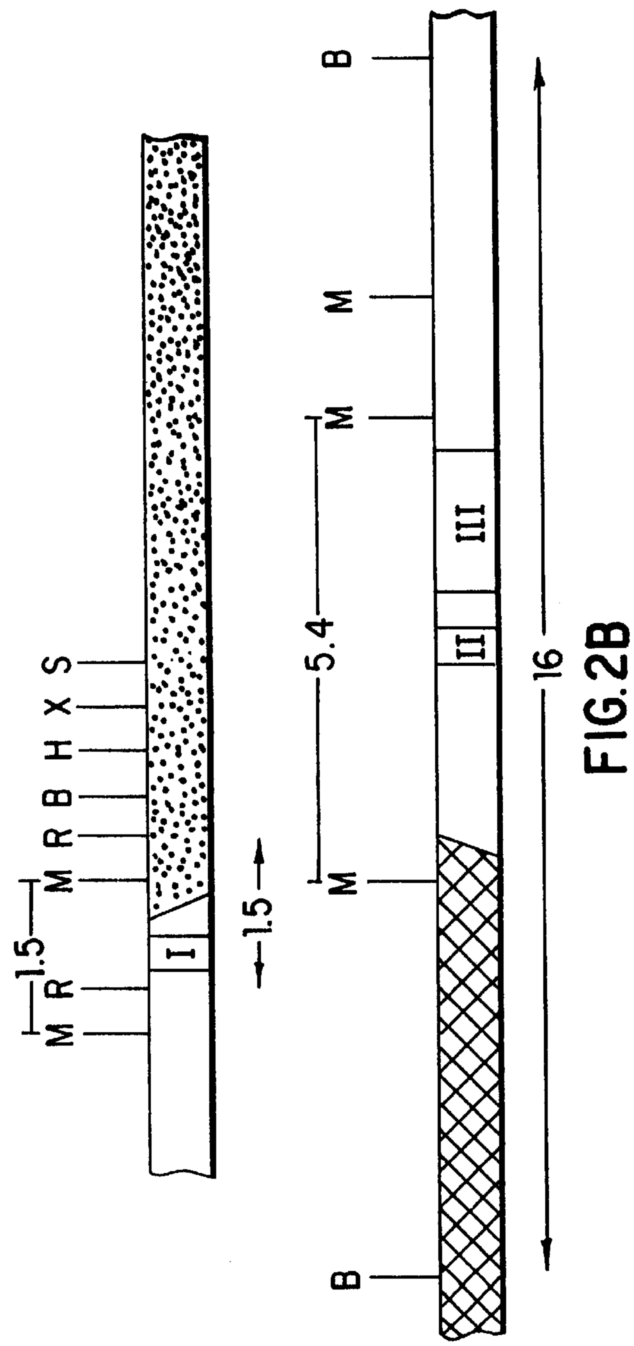

The DNA abnormality in parathyroid tumor M was initially characterized by Southern analysis of MspI digests using probes specific for the 5' and 3' regions in the PTH gene (see below), which revealed a unique, tumor-specific band. FIG. 1 illustrates these Southern blots of tumor M (T) and peripheral blood leukocyte (L) DNA pairs. MspI-digested DNA was probed with the 5' PTH gene probe (lanes 1, 2) and 3' PTH gene probe (lanes 3, 4). Squares indicate the normal gene (6.3 kb); arrows indicate the rearranged allele (1.5 kb in lane 1, 5.4 kb in lane 3). There is an MspI site within the DNA to which the 3' probe hybridizes (see FIG. 2*a*); therefore, a smaller band (2.2 kb) representing the most 3' section of the normal PTH gene is present in lanes 3 and 4. The intensities of the bands representing the abnormal allele were approximately equal to those representing the normal allele. Thus, in tumor M, as in tumor Y (Arnold et al., 1989), a clonal rearrangement of the PTH gene has occurred: in every tumor cell, one of the two alleles of the PTH gene remains normal but the other is. disrupted. FIG. 2(*a*) illustrates the normal PTH gene, with the positions of its three exons (Vasicek et al., Proc. Natl. Acad. Sci. USA 80:2127–2131, 1983), the 5' and 3' probes used in mapping and cloning, and the MspI sites indicated. In comparison, FIG. 2(*b*) shows the two fragments resulting from the rearrangement in tumor M: one consists of the 5' PTH gene sequences plus juxtaposed non-PTH DNA (stippled area), while the other consists of 3' PTH gene sequences plus juxtaposed non-PTH DNA (cross-hatched area). In each fragment, the location of the breakpoint is shown by a diagonal line. The locations of several restriction enzyme sites, determined by Southern blot analysis of tumor DNA, are indicated: EcoRI (R), BamHI (B), HindIII (H), XhoI (X), SstI (S), MspI (M). The locations and sizes of the 1.5 kb and 5.4 kb rearranged MspI fragments, (shown in FIG. 1) are indicated above each fragment. Below each fragment, lines ending in arrow tips depict the 1.5 kb and 16 kb cloned tumor DNA fragments. Analysis with multiple additional restriction enzymes indicated that the gene is separated into two parts, with the breakpoint located in the first intron (FIG. 2*b*). Consequently, upstream regulatory elements and the first, non-coding exon in the 5' fragment are separated from the coding sequences in the 3' fragment. Each PTH gene fragment remains internally intact (within the limits of sensitivity of restriction mapping), but has become juxtaposed to non-PTH DNA.

To identify the rearranged non-PTH DNA (shaded and cross-hatched areas in FIG. 2*b*), two DNA fragments containing PTH gene sequences plus breakpoint-adjacent DNA were cloned from tumor M DNA. One was a 16 kb BamHI fragment containing approximately 8 kb of non-PTH gene DNA adjacent to 8 kb of 3' PTH gene sequences (FIG. 2*b*). Genomic Southern blots of normal DNA probed with subclones spanning most of the 8 kb of non-PTH DNA showed diffuse smears that did not yield to attempts at competition with excess human DNA (Sealy et al., 1985). This indicated that the non-PTH DNA in the 16 kb fragment contained sequences highly repeated in the human genome, and precluded its chromosomal localization.

We also cloned a 1.5 kb EcoRI fragment containing approximately 1 kb of the PTH gene's 5' region plus 500 bp of juxtaposed non-PTH DNA (FIG. 2*b*). Probing normal human DNA blots with the subcloned 500 bp fragment demonstrated that it contained single-copy DNA; in situ hybridization and analysis of somatic cell hybrids revealed that the 500 bp fragment's normal chromosomal location is 11q13.

Figure 3:
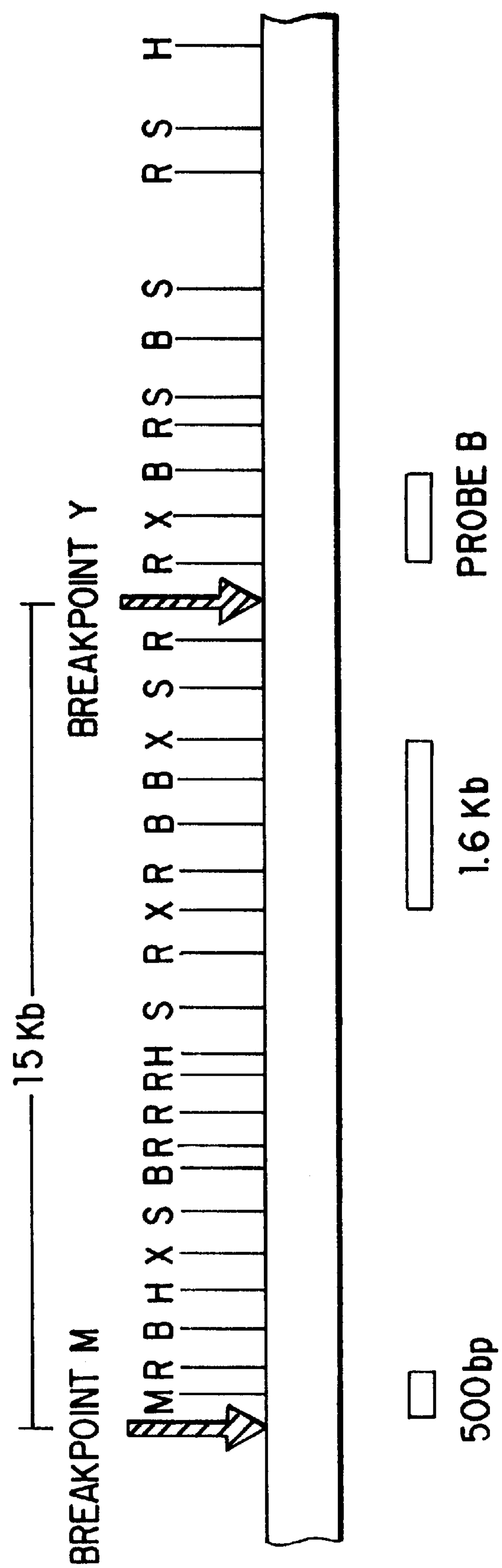
FIG. 3 is diagrammatic representation of the D11S287 region, indicating known restriction sites and the locations of the 500 bp fragment, the 1.6 kb XhoI fragment, and Probe B.

Hybridization of the 500 bp breakpoint-adjacent DNA fragment to an RNA blot of six parathyroid adenomas, including two with PTH gene rearrangements, was negative. To identify transcribed sequences near the breakpoint that could have been affected by the rearrangement, we walked along the chromosome by probing a normal human genomic library with the 500 bp subcloned fragment. We obtained a bacteriophage clone with a 14 kb insert, but Northern blot analyses revealed no hybridization of subclones spanning the entire insert. Mapping of the 14 kb insert showed that the 500 bp fragment was at one end, and demonstrated that the adjacent cloned DNA had a restriction map identical to that of the genomic DNA juxtaposed to tumor M's rearranged 5' PTH gene fragment. (Compare FIGS. 2*b* and 3). At the other end of the 14 kb insert was a 1.6 kb XhoI fragment (FIG. 3) identical in size to an XhoI fragment 1 kb from tumor Y's D11S287 breakpoint (Arnold et al., 1989). We subcloned these two independent 1.6 kb XhoI fragments (one from the above normal phage clone and one from a tumor Y-derived clone) and used them sequentially to probe blots of normal human genomic DNA digested with 7 restriction enzymes. With every enzyme, the two probes hybridized to precisely comigrating fragments. In addition, restriction maps of the two 1.6 kb fragments themselves were identical for all 6 enzymes used. Thus, the 1.6 kb XhoI fragment linked tumor M's breakpoint-adjacent DNA with that of tumor Y (D11S287), confirming that the 11q13 breakpoints in the two adenomas are both in the D11S287 region, separated by 15 kb. The composite restriction map of the unrearranged D11S287 region is shown in FIG. 3, in which restriction sites for the enzymes HindIII (H), BamHI (B), EcoRI (E), SacI (S), MspI (M) and XhoI (X) are indicated. The locations of the 500 bp fragment, the 1.6 kb XhoI fragment, and probe B are shown. This map is derived from the maps of the phage clones described above and by Arnold et al. (1989), and Southern blots of DNA from tumors M and Y.

Figure 4:
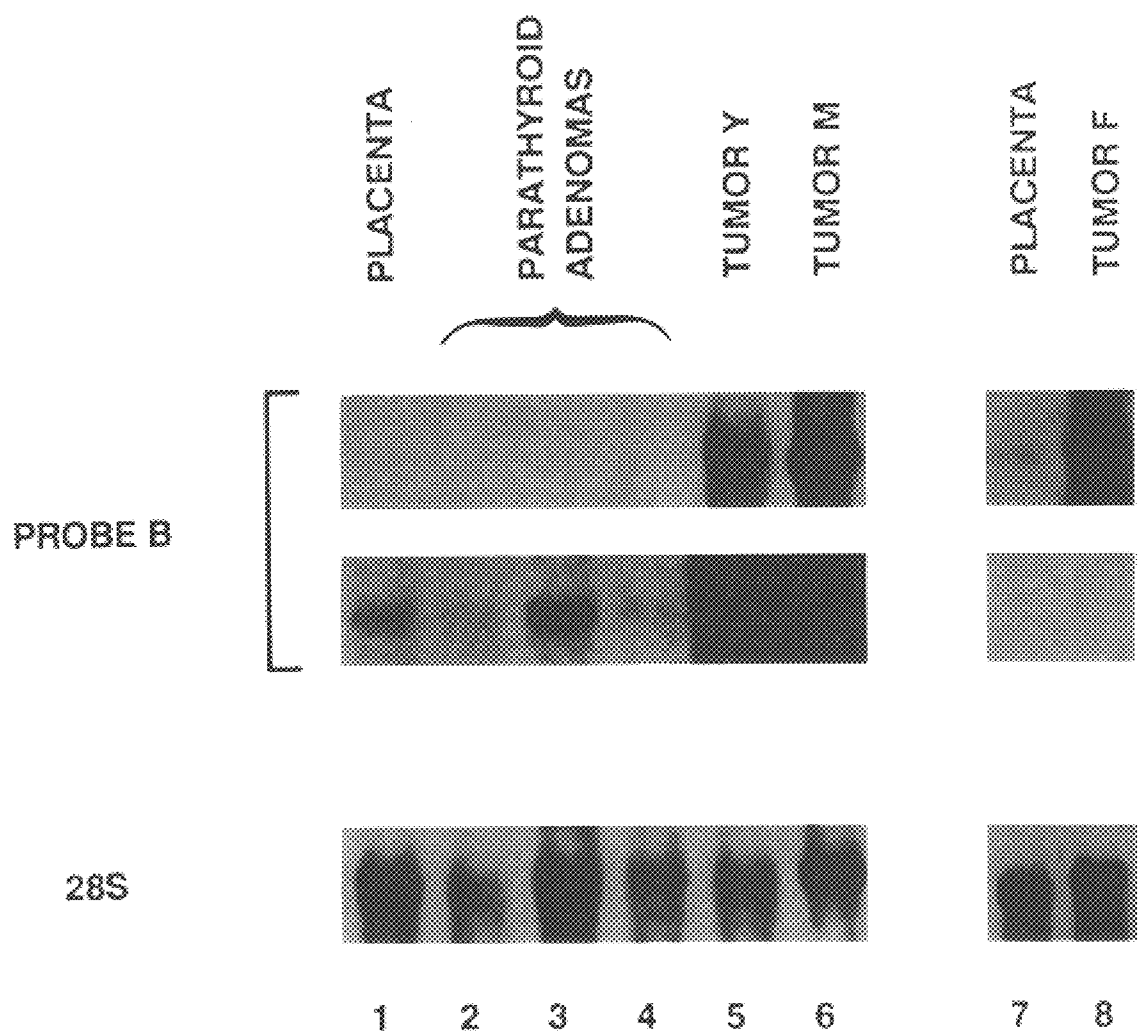
FIG. 4 is a Northern analysis of D11S287 expression in various cell types.

The proximity of the 11q13 breakpoints suggested that the rearrangements could have similar functional consequences. Because none of the DNA between the two tumors' breakpoints is transcribed in parathyroid cells, we looked for transcribed sequences distal to tumor Y's breakpoint. We used fragment B (FIG. 3), a breakpoint-adjacent DNA fragment from tumor Y, to probe a blot containing total RNA from human placenta, several parathyroid adenomas lacking PTH gene rearrangements, and tumors M and Y. We also hybridized probe B to another blot containing total RNA from placenta and from another parathyroid adenoma (tumor F) that was found recently to contain a clonal rearrangement of the PTH and D11S287 loci (Friedman et al., 1990); Southern blotting indicated that tumor F's rearrangement closely resembled tumor Y's. FIG. 4 presents the results of the Northern blots, in which 10 micrograms of total RNA was probed with Probe B (top panels), and with a 28S rRNA probe (bottom panels). Size determination was based on the migration of 28S rRNA. Lanes contain the following samples: lanes 1, 7: placenta; lanes 2, 3, 4: parathyroid adenomas without PTH gene or D11S287 rearrangements; lanes 5, 6, 8: tumors Y, M, and F. respectively; lanes 7 and 8 are a separate Northern filter. The middle panel is a longer exposure of lanes 1–6 in the top panel. In lanes 5 and 8 (tumors Y and F) a faint band was visible, larger than the highly-overexpressed 4.5 kb band, which was not seen in lane 6 (tumor M) (data not shown). Exposure times: top row (probe B): lanes 1–6, 17h; lanes 7 and 8, 12h; Middle row (probe B): all lanes, 52h; Bottom row (28S rRNA): all lanes, 1.5h. An approximately 4.5 kb transcript (slightly smaller than the 28S rRNA band) was seen in all lanes of FIG. 4. However, the intensity of the 4.5 kb band in tumors M, Y and F was roughly 15-fold greater than that in any of the other specimens. We demonstrated that the 4.5 kb band represents polyadenylated RNA by finding its intensity amplified in poly A+ RNA (data not shown).

Parathyroid adenoma M initially was identified as having an abnormal PTH gene during studies of the monoclonality of parathyroid adenomas (tumor 1 in Arnold et al., N. Eng. J. Med. 318:658–662, 1988). All tumor specimens were frozen in liquid nitrogen shortly after surgical removal. Extraction of high molecular weight DNA, restriction enzyme digestion and Southern blotting were performed as previously described (Arnold et al., N. Eng. J. Med., 309:1593–1599, 1983). Total RNA was isolated by the guanidinium thiocyanate/cesium chloride method, electrophoresed on a denaturing formaldehyde-agarose gel, and transferred to nitrocellulose or nylon filters (Sambrook et al., Molecular Cloning, A Laboratory Manual, 2nd edn. Cold Spring Harbor Laboratory Press, Cold Spring Harbor, N.Y., pp. 7.19–7.22, 7.37–7.39, 11.31–11.32, 1989). Hybridization conditions were similar to those used for Southern filters. Blots were washed at high stringency (0.1×SSC, 65°).

PTH gene fragments used as hybridization probes were the 775 bp BglII fragment (5' PTH probe) and the 2.6 kb SstI-EcoRI fragment (3' PTH probe) from pPTHg108 (Igarashi et al., Mol. Cell. Biol. 6:1830–1833, 1986) (FIG. 2*a*). The 500 bp fragment and probe B (FIG. 3) were subcloned into pUC-18 from the breakpoint-adjacent DNA of the phage clones containing the rearranged PTH gene fragment plus juxtaposed DNA from tumor M (see above), and tumor Y (Arnold et al., 1989), respectively. The 1.6 kb XhoI fragment from the 14 kb insert cloned from the normal human genomic library was also sub-cloned into pUC-18. The 1.6 kb Xhol fragment from tumor Y was subcloned from a λphage 2001 clone containing the 17 kb HindIII fragment of tumor Y's unrearranged D11S287 allele (Arnold et al., 1989). All the above probes were random-primed and labelled with [$^{32}$P]DATP (Feinberg & Vogelstein, Anal. Biochem. 132:6–13, 1983). The 28S RNA oligonucleotide was end-labelled with [$^{32}$P]dATP (Sambrook et al., 1989) and used to probe the Northern filters to control for the amount of high molecular weight RNA present in each lane.

To clone the rearranged 5' PTH gene fragment (FIG. 2*b*), an EcoRI library of tumor genomic DNA was constructed using the λZapII vector (Stratagene). This library was screened with the 5' PTH gene probe, and the rearranged allele was distinguished from the normal allele by size, as DNA blots predicted that the rearranged EcoRI fragment would be 1.5 kb in size, and the normal fragment 3.5 kb. One clone containing the rearranged gene was identified in $1\times10^6$ plaques that were screened.

To clone the rearranged 3' PTH gene fragment (FIG. 2*b*), a BamHI library of tumor genomic DNA was constructed in EMBL-3. Because restriction mapping indicated that both the normal and rearranged 3' PTH BamHI fragments were 16 kb in size, the library was screened with the 3' PTH probe (expected to hybridize to both the normal and rearranged PTH alleles) and then with the 5' PTH probe (expected to hybridize only to the normal allele). One clone containing the rearranged allele was identified in $6.5\times10^3$ plaques screened. As predicted, it contained 8 kb of 3' PTH gene sequences and 8 kb of newly-juxtaposed DNA. Most of this 8 kb was sub-cloned in roughly 2 kb units into pUC-18, and used to probe Southern filters of normal genomic DNA.

Prereassociation was performed by sonicating 1 mg of human placental genomic DNA and incubating it for 10–60 min with 50–100 ng of labelled repeat-containing subcloned DNA. This mix was then hybridized to a Southern filter containing normal human DNA using standard conditions.

The genomic library used to obtain the 14 kb insert was a partial Sau-3a digest of normal human DNA cloned into an EMBL-3 like vector (Clontech).

Chromosomal mapping using human-mouse somatic cell hybrids (Shows et al., Adv. Hum. Genet. 12:341–452, 1982;

Shows et al., Somatic Cell Mol. Genet. 10:315–318, 1984); Southern blotting (Naylor et al., J. Exp. Med. 57:1020–1027, 1983); and in situ hybridization (Zabel et al., Cytogenet. Cell Genet. 39:200–205, 1985; Nakai et al., Cytogenet. Cell Genet. 43:215–217, 1986) was performed as previously described.

Figure 5:
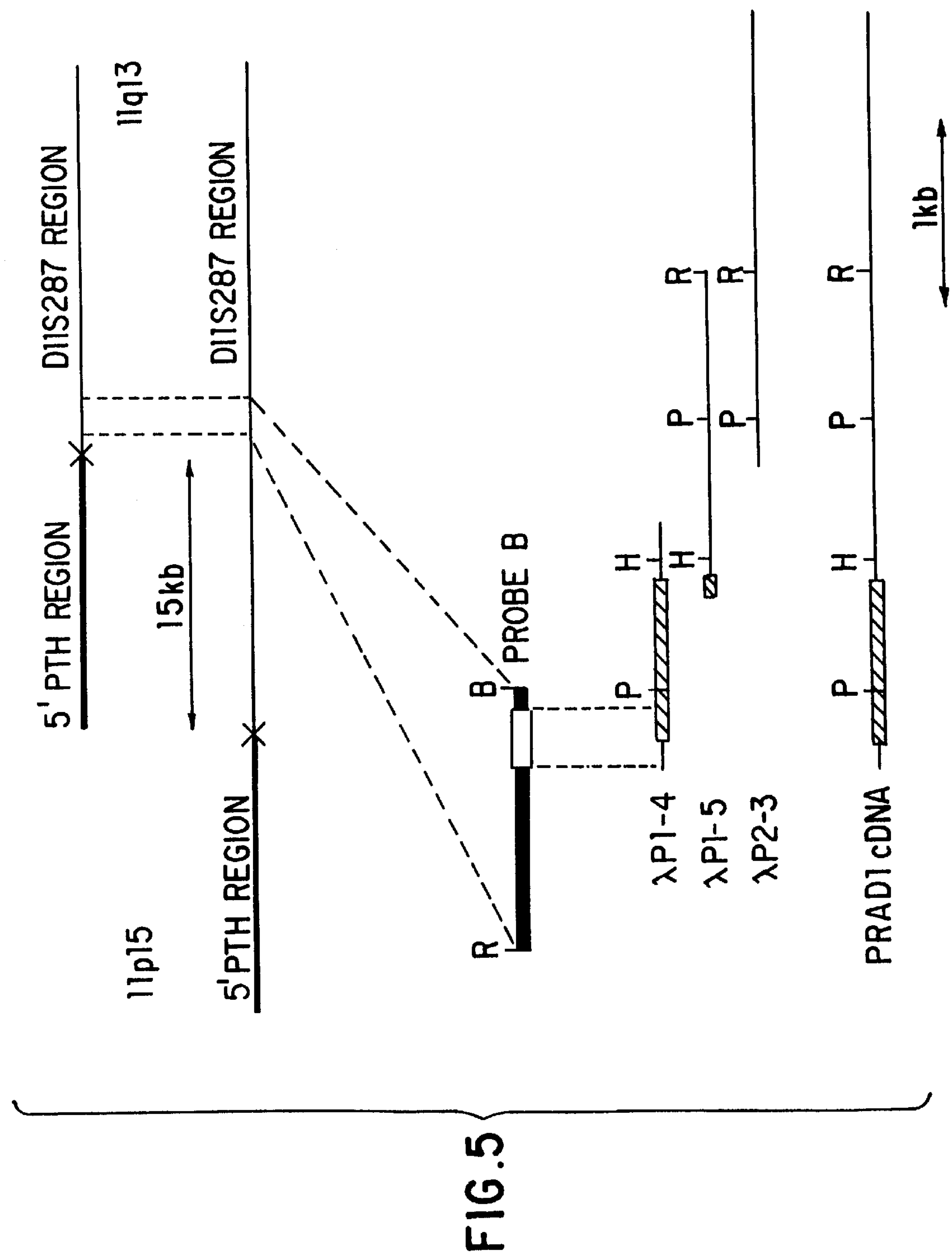
FIG. 5 is a diagrammatic representation of PTH/D11S287 rearrangements in two parathyroid adenomas, and the relative locations of Probe B and a series of cloned CDNA segments.

A λgt11 placental cDNA library (Clontech) was screened with radiolabeled Probe B. A clone denominated λP1-4 and another similar phage clone were isolated. Probe B and the insert of λP1-4 were sequenced. The region of genomic and cDNA overlap was followed in Probe B by a GT splice donor sequence in only one orientation, confirming hybridization data which had suggested transcription in the left to right orientation, as shown in FIG. 5. The next probe was made by polymerase chain reaction amplification of the 3' region of the λP1-4 cDNA insert, and used to rescreen the same library. From $5\times10^5$ pfu of this library, one of 16 positive clones, λP1-5, had an insert extending further downstream. The PstI/EcoRI fragment of λP1-5 was then used to rescreen the library, and 12 similar clones, the longest of which was λP2-3, were obtained. The sequence of the insert of λP2-3 revealed polyadenylation signals and a polyA stretch of 16 nucleotides in an appropriate position, consistent with the expected orientation. Standard methods for library screening and probe labeling were used (Davis et al., Basic Methods in Molecular Biology (Elsevier, New York, Amsterdam, London, 1986). These clones are illustrated in FIG. 5, together with a schematic representation of PTH/D11S287 rearrangements in two parathyroid adenomas. The 5' PTH region (11p15, thick lines) was juxtaposed to the D11S287 region (11q13, thin lines) in each of these adenomas. The breakpoints in the D11S287 region are 15 kb apart. Genomic Probe B is shown as a darkened box; whose open area represents the first exon of PRAD1. Also shown are restriction maps of the inserts of representative overlapping PRAD1 CDNA clones, λP1-4, λP1-5, and λP2-3; and the deduced restriction map of the PRAD1 cDNA. The coding region is shown as a crosshatched box. Scale of 1 kb is shown as arrows. Symbols used for restriction sites are: B, BamHI; E, EcoRI; H, HindIII; P, PstI.

The inserts of the clones λP1-4, λP1-5, and λP2-3 shown in FIG. 5, and of other independent clones, were subcloned into pGEM7Zf(+) (Promega). Sequences were obtained using the double-stranded DNA sequencing technique (dideoxy method) with modified T7 DNa polymerase (Sequenase; U.S. Biochemical Corporation), as described by the manufacturer. Several oligonucleotides were synthesized as internal primers to facilitate sequencing. The coding region was sequenced in both orientations and in at least two independent clones. Set forth in FIG. 6 are the nucleotide sequence and predicted. amino acid sequence of human PRAD1 cDNA (SEQ ID NO:1). Nucleotide numbers are on the right. Nucleotide 3495, shown as W, indicates A or T because the sequences of two independent clones did not agree. Nucleotide 4017 is shown as R, meaning A or G, for the same reason.

FIG. 7 illustrates sequence homology between the "cyclin box" region of the predicted PRAD1 protein (prad1) and that of A-type cyclins (human and clam cyclin A) (Swenson et al., Cell 47:861–870, 1986, and Wang et al., Nature 343:555–557, 1990); B-type cyclins (human cyclin B and S. pombe cdc13) (Pines et al., Cell 58:833–846, 1989; and Booher et al., EMBO J. 7:2321–2327, 1988), and one S. cerevisiae G1 cyclin (cln3) (Nash et al., EMBO J. 7:4335–4346, 1988; Cross et al., Mol. Cell. Biol. 8:4675–4684, 1988) Clam cyclin A and S. pombe cdc13 homologies with prad1 are representative of those found in their families; cln3 alignes with prad1 more closely than does cln1 or 2. Identical amino acids are shown as ¦. Conservative substitutions are shown as *. Alignment was made with the assistance of the BESTFIT program (Devereux et al., Nucl. Acids Res. 12:387–395, 1984) and conservative amino acids are grouped as follows: D, E, N, Q; H, K, R; A, G, P, S, T; I, L, M, V; F, W, Y. Amino acid numbers are on the right in this Figure.

Figure 8:
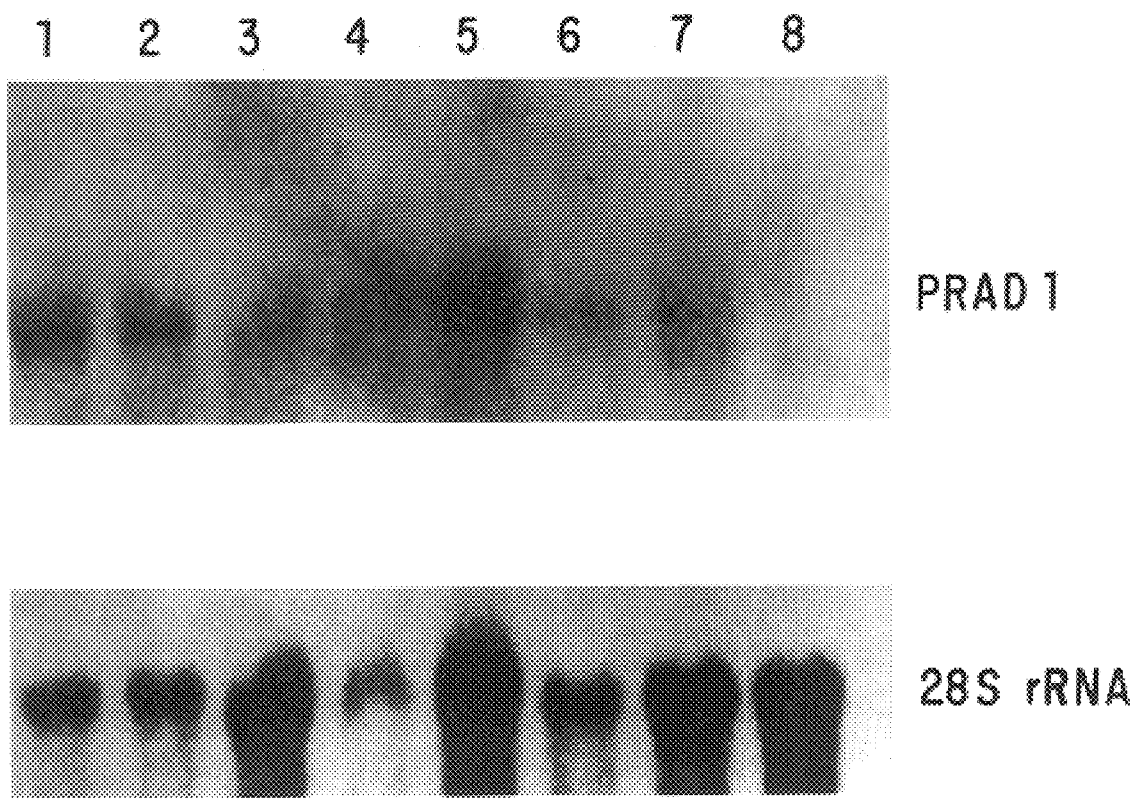
FIG. 8 is a Northern blot analysis of D11S287 [human PRAD1 (SEQ ID NO:1)] expression in various cell types.

RNAs were prepared for Northern blot analysis from the indicated tissues by standard procedures (Davis et al., 1986). 10 μg total RNA was loaded and separated on an agarose-formaldehyde gel, blotted onto nitrocellulose, and hybridized with Probe B or the 28S rRNA oligonucleotide. The filters were washed at high stringency (0.1×SSC, 60° C.) and autoradiographed. FIG. 8 illustrates a Northern blot analysis of total RNA from human thyroid (lane 1), human placenta (lane 2), bovine parathyroid (lane 3), bovine thyroid (lane 4), bovine lymph node (lane 5), bovine skeletal muscle (lane 6), murine heart (lane 7), and murine liver (lane 8). PRAD1 mRNA (shown in the upper panel) is approximately 4.5 kb in size, slightly smaller than the 28S rRNA; 28S rRNA hybridization is shown in the lower panel. FIG. 9(*a*) shows a Northern blot analysis of total RNA from HeLa S3 cells after release from G1/S block. Hela S3 cells (American Type Culture Collection), maintained in Dulbecco Modified Eagle Medium (DMEM, GIBCO) with 7% fetal bovine serum (FBS), were synchronized at the G1/S boundary by sequential thymidine-aphidicolin treatment (Heintz, et al., Mol. Cell. Biol. 3:539–550, 1983) with a slight modification. Log-phase cells were incubated in complete medium (DMEM with 7% FBS, penicillin G, and streptomycin) with addition of 2 mM thymidine (Sigma) for 12 h. After release from thymidine block by 3 washes with PBS, the cells were incubated for 10 h with 24 μM deoxycytidine (Sigma) and 24 μM thymidine, recovered by trypsinization, counted, and aliquoted equally ($5.0\times10^4$ cells/cm$^2$). Incubation with 5 μg/ml aphidicolin (Sigma) for 14 h was followed by release from G1/S block with 4 DMEM washes and incubation in complete medium. [$^3$H]Thymidine (NEN) was added to an aliquot 15 min before each indicated time point; a 30 min incubation and harvesting for trichloroacetic acid (TCA) precipitation followed. RNAs from parallel aliquots were extracted (Chomczynski et al., Anal. Biochem. 162:156–159, 1987) at the indicated times; time zero was just before release from aphidicolin. RNAs (5 μg per lane) were blotted onto nitrocellulose and sequentially hybridized with the PRAD1 λp1-4 cDNA insert, human H4 histone pF0108X (Pauli et al., Science 236:1308–1311, 1987), and a 28S rRNA oligonucleotide as described above. Human PRAD1 mRNA is shown in the upper panel of FIG. 9(*a*); H4 histone mRNA in the middle panel shows the pattern expected in well-synchronized cells (Heintz et al., 1983); and 28S rRNA is shown in the lower panel as a control for RNA loading. In FIG. 9(*b*) are compared the relative amounts of human PRAD1 mRNA (-●-), H4 histone mRNA (-○-), and [$^3$H]thymidine incorporation (-■-) of HeLa S3 cells after release from G1/S block. The signals of the blot shown in FIG. 9(*a*) were measured by densitometry and normalized to the 28S rRNA to produce the graph of FIG. 9(*b*).

Clam embryo interphase cell lysates lacking endogenous cyclins were prepared by adding 100 μM emetine during first mitosis, as described previously (Luca et al., J. Cell Biol. 109:1895–1909, 1989), followed by homogenization and centrifugation at 150,000×g. Aliquots of the supernatant were frozen in liquid nitrogen. [$^{35}$S]methionine-labeled prad1 was produced in a reticulocyte lysate in vitro translation system (Promega) according to manufacturer's instructions, by using aplasmid (denominated pP1-8) containing the λP1-4 insert in pGEM7Zf(+) (Promega). To produce prad1 in *E. coli*, pT4R-1 was constructed by insertion of the λP1-4 insert into the NcoI and BamHI sites of pET-3d (Studier et al., Meth. Enzym. 108:60–89, 1990). BL21(DE3) cells were transformed with pT4R-1, cultured, and treated with 0.4 mM isopropylthio-beta-galactosidase (IPTG) for 3 h to induce prad1 expression. The induced product was purified from cell culture as inclusion bodies (Gardella et al., J. Biol. Chem 265:15854–15859, 1990). On SDS-polyacrylamide gels, the apparent sizes of the in vitro translation product and the bacterially-expressed product were the same ($M_r$ 35kD). Rabbit anti-prad1 antisera were raised against a synthetic peptide corresponding to amino ID acids 9–37 of prad1. Antisera were assayed by immunoprecipitation of the in vitro translation product. Antisera specificity was shown by comparison with normal rabbit serum and by successful competition with the (9–37) peptide (data not shown).

Thawed clam embryo lysate (16.5 $\mu$l) and bacterially-expressed prad1 (5.5 $\mu$l) were mixed and incubated at 18° C. for 30 min before transfer to 4° C., dilution with 4 volumes of buffer A (50 mM Tris pH 7.4, 150 mM NaCl, 5 mM EDTA, 5 mM EGTA, 1 mM ammonium molybdate) and addition of $p13^{suc1}$- or protein A-Sepharose, followed by mixing for 1 h. Beads were then pelleted and washed in buffer A+0.5% Tween-20; in buffer B (50 mM Tris pH 7.4, 1.0 M NaCl, 5 mM EDTA, 5 mM EGTA, 1 mM molybdate, 0.5% Tween-20); and finally in buffer A without Tween-20, all at 4° C. Washed beads were boiled in SDS sample buffer for 3 min and the supernatant split into three samples for electrophoresis. Gels were silver stained or blotted onto nitrocellulose filters and reacted with rabbit antibodies generated against bacterially-expressed, full-length S. pombe cdc2 protein or prad1 peptide as above. Antibody binding was visualized by alkaline phosphatase-linked secondary antibodies, according to the manufacturer's directions (Promega). FIG. 10 demonstrates that prad1 protein added to clam embryo cell lysates binds to $p13^{suc1}$-Sepharose beads and activates histone H1 kinase activity. Bacterially expressed prad1 was incubated with a clam embryo interphase lysate lacking endogenous cyclins A and B. The lysates were then mixed with $p13^{suc1}$- or protein A-Sepharose beads. The bound material was eluted, electrophoresed and either silver stained (a) or immunoblotted with anti-prad1 antiserum (b) or anti-cdc2 antiserum (c). Lane M shows molecular weight markers (from top to bottom) of 116, 94, 68, 56, 40, and 31 kD. Lane 1 shows whole clam embryo interphase lysate plus 18 ng prad1 protein. Lanes 2, 3, 4, 5, and 6 represent clam embryo lysate to which 0, 18, 45, 225, or 18 ng of prad1, respectively, were added; these mixes were then assayed for material binding to $p_{13}^{suc1}$-Sepharose (lanes 2–5) or protein A-Sepharose (lane 6) beads. Lane 7 shows bacterially-expressed prad1. Arrows indicate the positions of prad1 and cdc2 marker proteins.

Equal volumes of clam embryo interphase lysate and reticulocyte lysate containing [$^{32}$P]-labeled kinase products were then examined by SDS-PAGE, followed by autoradiography. Synthetic clam cyclins A and B (Westendorf et al., g. Cell Biol. 108:1431–1444; Swenson et al., Cell 47:861–870, 1986) and prad1 mRNAs were transcribed and translated as described above. Translation product (3 $\mu$l) and clam embryo lysate (3 $\mu$l) were mixed. Samples were frozen immediately in liquid nitrogen. The remainder was incubated for 30 min at 18° C. and then frozen. Samples were diluted with 1 volume of ice-cold buffer A, thawed on ice, and mixed with an equal volume of kinase mix (40 mM Hepes pH 7.3, 20 mM $MgCl_2$, 10 mM EGTA, 0.2 mg/ml histone H1, 10 $\mu$M cAMP-dependent kinase inhibitor (Sigma), 0.5 mCi/ml [γ-$^{32}$P]ATP and incubated at 23° C. for 10 min. Double-strength SDS sample buffer was then added and the entire mix was analyzed by SDS-PAGE followed by autoradiography, as shown in FIG. 10(*d*).

What is claimed is:

1. A transgenic mouse whose genome comprises a transgene comprising a DNA sequence encoding PRAD1 operably linked to a heterologous tissue-specific promoter, wherein said DNA sequence is expressed at elevated levels in at least some cells of a tissue such that said mouse develops neoplasia or hyperplasia in said tissue.

2. The transgenic mouse of claim 1, wherein said PRAD1 is endogenous to said mouse.

3. The transgenic mouse of claim 1, wherein said PRAD1 is human PRAD1.

4. A cell isolated from the transgenic mouse of claim 1, wherein said cell comprises a transgene comprising a DNA sequence encoding PRAD1 operably linked to a heterologous tissue-specific promoter.

5. The transgenic mouse of claim 1, wherein said at least some cells are selected from the group consisting of breast cells, squamous cells, B-lymphoid cells and parathyroid cells.

6. The transgenic mouse according to claim 1, wherein said tissue specific promoter is selected from the group consisting of a mouse mammary tumor virus-long terminal repeat (MMTV-LTR) promoter and a metallothionein promoter.

7. The transgenic mouse according to claim 1, wherein said tissue is breast tissue and said tissue specific promoter is a mouse mammary tumor virus-long terminal repeat (MTV-LTR) promoter.

* * * * *

UNITED STATES PATENT AND TRADEMARK OFFICE

CERTIFICATE OF CORRECTION

PATENT NO. : 6,107,541
DATED : August 22, 2000
INVENTOR(S) : Andrew Arnold

It is certified that error appears in the above-identified patent and that said Letters Patent is hereby corrected as shown below:

Title page, Item [54] and Column 1, line 1,
Please change the title of the invention by deleting "PRAD1 TRANSGENIC MICE" and inserting therefor -- PRAD1 (CYCLIN D1) TRANSGENIC MICE --.

Signed and Sealed this

Ninth Day of September, 2003

JAMES E. ROGAN
*Director of the United States Patent and Trademark Office*